US009333276B2

(12) United States Patent
Guelcher et al.

(10) Patent No.: US 9,333,276 B2
(45) Date of Patent: May 10, 2016

(54) BONE/POLYURETHANE COMPOSITES AND METHODS THEREOF

(75) Inventors: Scott A. Guelcher, Franklin, TN (US); Subhabrata Bhattacharyya, Metuchen, NJ (US); Katarzyna Jadwiga Zienkiewicz, Nashville, TN (US); Shaun A. Tanner, Charlottesville, VA (US); Jerald E. Dumas, Nashville, TN (US)

(73) Assignees: Vanderbilt University, Nashville, TN (US); Warsaw Orthopedic, Inc., Warsaw, IN (US)

( * ) Notice: Subject to any disclaimer, the term of this patent is extended or adjusted under 35 U.S.C. 154(b) by 85 days.

(21) Appl. No.: 12/608,850

(22) Filed: Oct. 29, 2009

(65) Prior Publication Data
US 2010/0112032 A1 May 6, 2010

Related U.S. Application Data

(60) Provisional application No. 61/109,892, filed on Oct. 30, 2008, provisional application No. 61/120,836, filed on Dec. 8, 2008, provisional application No. 61/242,758, filed on Sep. 15, 2009.

(51) Int. Cl.
*A61L 27/44* (2006.01)
*A61L 27/56* (2006.01)

(52) U.S. Cl.
CPC *A61L 27/44* (2013.01); *A61L 27/56* (2013.01)

(58) Field of Classification Search
CPC .......... A61L 27/44; A61L 27/56; C08L 75/04
See application file for complete search history.

(56) References Cited

U.S. PATENT DOCUMENTS

| | | | |
|---|---|---|---|
| 4,743,259 A | 5/1988 | Bolander et al. | |
| 4,880,610 A | 11/1989 | Constantz | |
| 4,882,149 A | 11/1989 | Spector | |
| RE33,161 E | 2/1990 | Brown et al. | |
| 4,902,296 A | 2/1990 | Bolander et al. | |
| RE33,221 E | 5/1990 | Brown et al. | |
| 5,034,059 A | 7/1991 | Constantz | |
| 5,047,031 A | 9/1991 | Constantz | |
| 5,053,212 A | 10/1991 | Constantz | |
| 5,129,905 A | 7/1992 | Constantz | |
| 5,149,368 A | 9/1992 | Liu et al. | |
| 5,262,166 A | 11/1993 | Liu et al. | |
| 5,290,558 A | 3/1994 | O'Leary et al. | |
| 5,336,264 A | 8/1994 | Constanz | |
| 5,417,975 A | 5/1995 | Lussi et al. | |
| 5,462,722 A | 10/1995 | Liu et al. | |
| 5,507,813 A | 4/1996 | Dowd et al. | |
| 5,525,148 A | 6/1996 | Chow et al. | |
| 5,531,791 A * | 7/1996 | Wolfinbarger, Jr. ........ 623/23.63 |
| 5,542,973 A | 8/1996 | Chow et al. | |
| 5,573,771 A | 11/1996 | Geistlich et al. | |
| 5,578,662 A | 11/1996 | Bennett | |
| 5,605,713 A | 2/1997 | Boltong | |
| 5,650,176 A | 7/1997 | Lee et al. | |
| 5,717,006 A | 2/1998 | Daculsi et al. | |
| 5,800,899 A * | 9/1998 | Sandvig et al. ................. 428/96 |
| 5,899,939 A | 5/1999 | Boyce et al. | |
| 5,948,386 A | 9/1999 | Katti et al. | |
| 6,001,394 A | 12/1999 | Daculsi et al. | |
| 6,002,065 A | 12/1999 | Constantz | |
| 6,066,681 A | 5/2000 | Kaplan | |
| 6,123,731 A | 9/2000 | Boyce et al. | |
| 6,123,781 A | 9/2000 | Shimazawa | |
| 6,206,957 B1 | 3/2001 | Driessens et al. | |
| 6,207,767 B1 | 3/2001 | Bennett | |
| 6,294,041 B1 | 9/2001 | Boyce et al. | |
| 6,294,187 B1 | 9/2001 | Boyce et al. | |
| 6,306,177 B1 | 10/2001 | Felt | |
| 6,332,779 B1 | 12/2001 | Boyce et al. | |
| 6,339,130 B1 | 1/2002 | Bennett | |
| 6,376,742 B1 | 4/2002 | Zdrahala | |
| 6,399,693 B1 | 6/2002 | Brennan et al. | |

(Continued)

FOREIGN PATENT DOCUMENTS

| | | |
|---|---|---|
| WO | 9819718 | 5/1998 |
| WO | 2004009227 | 1/2004 |

(Continued)

OTHER PUBLICATIONS

Huntsman, "Polyurethane Product Line", 2013.*
Adhikari et al., Biomaterials 2008;29(28):3762-70.
Baker et al., Plast Reconstr Surg 2002;109:1789-1796.
Bennett S, Connolly K, Lee DR, Jiang Y, Buck D, Hollinger JO, Gruskin EA. Initial biocompatibility studies of a novel degradable polymeric bone substitute that hardens in situ. Bone 1996; 19(1, Supplement):101S-107S.
Bonzani et al., Biomaterials 2007;28:423-33; Hafeman et al., Pharm Res 2008;25(10):2387-99.

(Continued)

*Primary Examiner* — Ali Soroush
(74) *Attorney, Agent, or Firm* — Stites & Harbison PLLC; Richard S. Myers, Jr.

(57) ABSTRACT

Present inventions present composites of bone particles and polyurethane(s), as well as methods of making such composite and uses thereof. A porous composite comprises a plurality of bone particles; and polyurethanes with which the bone particles are combined. To prepare a porous composite, a composition comprise a plurality of bone particles, polyurethane precursors including polyisocyanate prepolymers and polyols, water and catalyst. A composition is either naturally moldable and/or injectable, or it can be made moldable and/or injectable. After implantation or injection, a composition may be set to form a porous composite that provides mechanical strength and supports the in-growth of cells. Inventive composites have the advantage of being able to fill irregularly shape implantation site while at the same time being settable to provide the mechanical strength for most orthopedic applications.

32 Claims, 13 Drawing Sheets

(56) References Cited

U.S. PATENT DOCUMENTS

| | | | |
|---|---|---|---|
| 6,696,073 | B2 | 2/2004 | Boyce et al. |
| 7,291,345 | B2 | 11/2007 | Winterbottom et al. |
| 7,985,414 | B2 | 7/2011 | Knaack et al. |
| 8,002,843 | B2 | 8/2011 | Knaack et al. |
| 8,425,893 | B2 | 4/2013 | Knaack et al. |
| 2003/0036800 | A1* | 2/2003 | Meredith .................. 623/23.63 |
| 2003/0144743 | A1 | 7/2003 | Edwards et al. |
| 2004/0146543 | A1 | 7/2004 | Shimp et al. |
| 2005/0013793 | A1 | 1/2005 | Beckman |
| 2005/0031578 | A1* | 2/2005 | Deslauriers et al. ....... 424/78.27 |
| 2005/0238683 | A1 | 10/2005 | Adhikari et al. |
| 2006/0034769 | A1 | 2/2006 | Kohn et al. |
| 2006/0216323 | A1 | 9/2006 | Knaack et al. |
| 2007/0190108 | A1 | 8/2007 | Datta et al. |
| 2007/0191963 | A1 | 8/2007 | Winterbottom et al. |
| 2007/0299151 | A1 | 12/2007 | Guelcher et al. |
| 2008/0069852 | A1* | 3/2008 | Shimp et al. .................. 424/423 |
| 2009/0130174 | A1 | 5/2009 | Guelcher et al. |
| 2009/0221784 | A1 | 9/2009 | Guelcher et al. |
| 2010/0068171 | A1 | 3/2010 | Guelcher et al. |
| 2010/0112032 | A1 | 5/2010 | Guelcher et al. |
| 2010/0247672 | A1 | 9/2010 | Guelcher et al. |
| 2010/0297082 | A1 | 11/2010 | Guelcher et al. |
| 2011/0237704 | A1 | 9/2011 | Guelcher et al. |
| 2012/0183622 | A1 | 7/2012 | Guelcher et al. |

FOREIGN PATENT DOCUMENTS

| | | |
|---|---|---|
| WO | 2004069890 | 8/2004 |
| WO | 2006055261 | 5/2006 |
| WO | 2007084609 | 7/2007 |
| WO | 2007123536 | 11/2007 |
| WO | WO-2007/123536 A1 * | 11/2007 |
| WO | 2009026387 | 2/2009 |
| WO | 2009033088 | 3/2009 |
| WO | 20090033102 | 3/2009 |
| WO | 2010059389 | 5/2010 |
| WO | 2011075183 | 6/2011 |
| WO | 2012134540 | 10/2012 |
| WO | 2014026052 | 2/2014 |

OTHER PUBLICATIONS

Boyce et al., Cellular Penetration and Bone Formation Depends Upon Allograft Bone Fraction in a Loadbearing Composite Implant. 2005. p. 133.

Chim et al., J Craniofac Surg 2009;20:29-33.

Clarkin et al., J Mater Sci: Mater Med 2009;20:1563-1570.

Ferrari and co-workers' in Ferrari RJ, Sinner JW, Bill JC, Brucksch WF. Compounding polyurethanes: Humid aging can be controlled by choosing the right intermediate. Ind. Eng. Chem. 1958;50(7):1041-1044.

Gorna et al., J Biomed Mater Res Pt A 2003;67A(3):813-27.

Guelcher et al., Tissue Eng 2006;12(5):1247-1259.

Guelcher et al., Tissue Engineering 2007;13(9):2321-2333.

Guelcher, Tissue Engineering: Part B, 14 (1) 2008, pp. 3-17.

Hafeman et al., Pharmaceutical Research 2008;25(10):2387-99.

Hasegawa et al., Biomaterials 2006;27:1327-1332.

Hollier et al., Clin Plastic Surg 2004;31:423-428.

Hooper, et al., J. Bioactive and Compatible Polymers, 1995, 10:327-340.

Hurley, et al., Milit. Med. 1957, 101-104.

James et al., Biomaterials 20:2203-2213, 1999.

Karageorgiou et al., Biomaterials 26:5474-5491, 2005.

Kershaw, Pharm. J. 6:537, 1963.

Klaitwatter et al., J. Biomed. Mater. Res. Symp. 2:161, 1971.

Lewandrowski, et al., J. Biomed. Mater. Res., 1996, 31:365-372.

Lewis et al., J Biomed Mater Res Part B : Appl Biomater 2007;81B:371-386.

Malinin et al., Open Orthop J 2007;1:19-24.

Moreira-Gonzalez et al., J Craniofac Surg 2003;14:144-153.

Murphy et al., Tissue Engineering 8(1):43-52, 2002.

Neuendorf et al., Acta Biomater 2008;4:1288-1296.

Oertel, Günter, ed., Polyurethane Handbook, Hanser Gardner Publications, Inc. Cincinnati, Ohio, 99-108 (1994).

Pulapura, et al., Biopolymers, 1992, 32: 411-417.

Reddi, et al., Proc. Nat. Acad. Sci., 1972, 69:1601-1605.

Simmons, et al, Biotechnol. Appl. Biochem., 1993, 17:23-29.

Skarja et al., J App Poly Sci 2000;75:1522-34.

Storey at el., Journal of Polymer Science, Part A: Polymer Chemistry 1994;32(12):2345-2363.

Szycher, M, Szycher's Handbook of Polyurethanes, CRC Press, New York, New York, (1999).

Zhang J-Y, Beckman EJ, Piesco NJ, Agarwal S. A new peptide-based urethane polymer: synthesis, biodegradation, and potential to support cell growth in vitro. Biomaterials 2000;21 :1247-1258.

Zhang J, Doll B, Beckman J, Hollinger JO. Three—dimensional biocompatible ascorbic acid-containing scaffold for bone tissue engineering. Tissue Engineering 2003;9(6)1 143-1157.

Zhang J, Doll B, Beckman E, Hollinger JO. A biodegradable polyurethane-ascorbic acid scaffold for bone tissue engineering. J. Biomed. Mater. Res. 2003;67A(2):389-400.

Zhang J-Y, Beckman EJ, Hu J, Yuang G-G, Agarwal S, Hollinger JO. Synthesis, biodegradability, and biocompatibility of lysine diisocyanate-glucose polymers. Tissue Engineering 2002;8(5):771-785.

* cited by examiner

BONE/POLYURETHANE COMPOSITES AND METHODS THEREOF

CROSS REFERENCES OF RELATED APPLICATIONS

The present application claims priority under 35 U.S.C. §119(e) to U.S. provisional patent applications, U.S. Ser. No. 61/109,892, filed Oct. 30, 2008; U.S. Ser. No. 61/120,836, filed Dec. 8, 2008; and U.S. Ser. No. 61/242,758, filed Sep. 15, 2009, each of which is incorporated herein by reference.

GOVERNMENT SUPPORT

This invention was made with support from the Rutgers-Cleveland Clinic Consortium in the Armed Forces Institute of Regenerative Medicine, which is funded by Department of Defense (W81XWH-08-2-0034). This work was also supported by the National Science Foundation through a CAREER award to SAG (DMR0847711), and by the Center for Military Biomaterials through the Department of Defense (W81XWH-04-2-0031).

BACKGROUND

Bone is a composite material composed of impure hydroxyapatite, collagen, and a variety of non-collagenous proteins, as well as embedded and adherent cells. Bone can be processed into an implantable biomaterial, such as an allograft, for example, by removing the cells, leaving behind the extracellular matrix. The processed bone biomaterial can have a variety of properties, depending upon the specific processes and treatments applied to it, and may incorporate characteristics of other biomaterials with which it is combined. For example, bone-derived biomaterials may be processed into load-bearing mineralized grafts that support and integrate with the patient's own bone or may alternatively be processed into soft, moldable, or flowable demineralized bone biomaterials that have the ability to induce a cellular healing response.

The use of bone grafts and bone substitute materials in orthopedic medicine is well known. While bone wounds can regenerate without the formation of scar tissue, fractures and other orthopedic injuries take a long time to heal, during which the injured bone is unable to support physiologic loading. Metal pins, screws, and meshes are frequently needed to replace the mechanical functions of injured bone. However, metal is significantly stiffer than bone. Use of metal implants may result in decreased bone density around the implant site due to stress shielding. Furthermore, most metal implants are permanent and unable to participate in physiological remodeling.

Bone's cellular healing processes, through bone tissue formation by osteoblast cells coordinated with bone and graft resorption by osteoclast cells, permit bone grafts and certain bone substitute materials to remodel into endogenous bone that is almost indistinguishable from the original. However, the use of bone grafts is limited by the available shape and size of grafts and the desire to optimize both mechanical strength and degradation rate. Variations in bone size and shape among patients (and donors) also make bone grafts a less optimal substitute material. Bone substitute materials and bone chips are quickly remodeled but cannot immediately provide mechanical support, while cortical bone grafts can support physiological stresses but remodel slowly.

Thus, it is desirable to have a biomaterial for structural grafts that may be produced in larger quantities than grafts derived solely from bone and that may be fabricated or molded into shapes without being limited by the shape of the originating tissue. It is also desirable to have injectable bone graft materials that may be implanted using minimally invasive techniques.

SUMMARY

The invention relates to injectable and/or moldable composites/compositions including at least bone particles and polyurethanes, methods of making such composites, methods of using such composites in orthopedic applications and various related compositions. The present invention provides porous composites which, when implanted or injected, promote cellular infiltration from adjacent osseous tissues, thus accelerating the remodeling process. Inventive composites comprise bone particles and polymers, such as a biocompatible polyurethane, and may further comprise additional components. The present invention also provides compositions, methods and processes that can be used for the preparation of such composites. The invention also provides methods and kits for making and/or using such inventive porous materials.

In some aspects, the present invention provides compositions and composites including a plurality of particles of an inorganic material, a bone substitute material, a bone-derived material, or any combination thereof, and a polymer with which the particles are combined. More specifically, in one aspect, the invention features a composite including allograft bone and biodegradable polyurethane (PUR). In some embodiments, a provided composite has a porosity of at least 30%.

A composition of particles and polymer is naturally moldable and/or injectable, or the composite can be made moldable or injectable such as by heating or by the addition of a solvent. Compositions may range from a thick, flowable liquid to a moldable, dough-like substance. In some embodiments, a composition has a low enough viscosity to be suitable for injection. In come embodiments, a composition is workable so that it can be molded into an implantation site. Once cured, a composition may result in a porous composite including bone particles and polyurethane. In some embodiments, a composition may include bone particles and a reactive liquid. Such a reactive liquid can be a two-component composition for polyurethane include polyisocyanates, polyols, water and catalyst, and optionally additional components such as a stabilizer, a porogen, a plasticizer, a chain extender, a wetting agent, etc. In some embodiments, a composition may include bioactive agents to deliver such as antibiotics, growth factors, etc.

In some embodiments, provided porous composites have a porosity of at least about 30%, at least about 40%, at least about 50%, at least about 60%, at least about 70%, at least about 80%, at least about 90% or more than 90%. Porous composites of the present inventions may comprise pores or channels which, after implantation or injection, can support the in-growth of cell and/or the formation or remodeling of bone.

In some embodiments, provided porous composites have a bone weight percentage of between about 30 wt % and about 90 wt %. For example, a weight percentage of bone particles may be about 30 wt %, about 40 wt %, about 45 wt %, about 50 wt %, about 55 wt %, about 60 wt %, about 70 wt %, about 80 wt %, 90 wt % or between any weight percentages of above. In some embodiments, a volume percentage of bone particles in composite in accordance with the present invention may be about 30 vol %, 35 vol %, 40 vol %, 50 vol %, 60 vol %, 70 vol % or between any volume percentages of above.

Bone particles in a composite used in the present invention may have a variety of shapes including spheroidal, plate, fiber, cuboidal, sheet, rod, ellipsoidal, string, elongated, polyhedral, and mixtures thereof. Particles in the composite have a mean size of about 10 to about 1000 microns in diameter, for example, a mean size of about 20 to about 800 microns in diameter. Smaller or larger irregularly shaped particles may also be found in composites. In certain embodiments, at least about 90% of the particles have a mean size of about 100 microns to about 1000 microns in their greatest dimension.

Polyurethane components used in preparing inventive composites may be selected from monomers, pre-polymers, oligomers, polymers, cross-linked polymers, partially polymerized polymers, partially cross-linked polymers, and any combinations thereof. For example, a composition may include polyurethane precursors. In some embodiments, polyurethane precursors include polyisocyanates prepolymers and polyols. In certain embodiments, polyisocyanates prepolymers may be prepared by reacting isocyanates with polyols. In certain embodiments, a polyol may include PEG.

Polyisocyanates or multi-isocyanate compounds for use in the present invention include aliphatic polyisocyanates. Exemplary aliphatic polyisocyanates include, but are not limited to, lysine diisocyanate, an alkyl ester of lysine diisocyanate (for example, a methyl ester or an ethyl ester), lysine triisocyanate, hexamethylene diisocyanate, isophorone diisocyanate (IPDI), 4,4'-dicyclohexylmethane diisocyanate ($H_{12}MDI$), cyclohexyl diisocyanate, 2,2,4-(2,2,4)-trimethylhexamethylene diisocyanate (TMDI), dimers prepared form aliphatic polyisocyanates, trimers prepared from aliphatic polyisocyanates and/or mixtures thereof. In some embodiments, hexamethylene diisocyanate (HDI) trimer sold as Desmodur N3300A may be a polyisocyanate utilized in the present invention.

In some embodiments, polyols are polyester polyols. In some embodiments, polyester polyols may include poly(ethylene adipate), poly(ethylene glutarate), poly(ethylene azelate), poly(trimethylene glutarate), poly(pentamethylene glutarate), poly(diethylene glutarate), poly(diethylene adipate), poly(triethylene adipate), poly(1,2-propylene adipate), mixtures thereof, and/or copolymers thereof. In some embodiments, polyester polyols can include, polyesters prepared from caprolactone, glycolide, D, L-lactide, mixtures thereof, and/or copolymers thereof. In some embodiments, polyester polyols can, for example, include polyesters prepared from castor-oil.

In some aspects, the present invention features methods including contacting bone particles with precursors of polyurethane to form porous composites. Water used in a composition may act as a blowing agent to generate a porous composite.

In some aspects, the invention provides methods of administering an inventive composite and/or composition to a subject in need thereof. Among other things the invention provides composites, for example, comprising bone particles and polyurethanes, for use in medicine. Inventive composites are useful in orthopedic medicine. A composite may be used to repair a fracture or other bony defect in a subject's bone. A composite may be used as bone void fillers. A method includes providing a flowable or moldable composition of a polyurethane, a plurality of bone particles and any additional components; administering the composition or composite to a subject in need thereof; and resulting in a porous composite to set in situ. Before administration, the composite may be made flowable or moldable, for example, by heating the composite or adding a solvent to the composite. A composite may be administered into an implantation site (e.g., a bony defect) followed by setting the composite. A composite may be allowed to remain at a target site providing the strength desired while at the same time promoting healing of the bone and/or bone growth. Polymer components of a composite may be degraded or be resorbed as new bone is formed at the implantation site. In some embodiments, a composite may be resorbed over approximately 1 month to approximately 6 years. In some embodiments, a porous composite may start to be remodeled in as little as a week as the composite is infiltrated with cells or new bone in-growth. The remodeling process may continue for weeks, months, or years.

In some embodiments, the present invention provides kits for the treatment of bone. A kit includes a composition including a plurality of bone particles and polyurethane with which the particles are combined. In some embodiments, a kit may include a composition being contained within a delivery system for delivering the composite by injection (e.g., a syringe). A kit may also include a high pressure injection device for implanting composition of higher viscosity. A kit may also include components of the composite packaged separately for mixing just prior to implantation or injection. In some embodiments, components of a composition used in accordance with the present invention is sterilely packaged separately. A kit may also include a heating apparatus for warming the composite to a temperature where it is moldable. A kit may also include a solvent, a diluent, or pharmaceutically acceptable excipient for combining with the composite. A kit may further include instructions for using the composite.

Embodiments may include one or more of the following features or advantages. Composites can allow and encourage direct boney in-growth and remodeling, which can improve patient outcome. Composites can be formed into a variety of shapes and sizes. Composite can be porous as-prepared and/or the porosity of the composite can change (e.g., increase) over time to support in-growth of bone.

Other aspects, features and advantages will be apparent from the description of the following embodiments and from the claims.

DEFINITIONS

The term "bioactive agent" is used herein to refer to compounds or entities that alter, promote, speed, prolong, inhibit, activate, or otherwise affect biological or chemical events in a subject (e.g., a human). For example, bioactive agents may include, but are not limited to osteogenic, osteoinductive, and osteoconductive agents, anti-HIV substances, anti-cancer substances, antibiotics, immunosuppressants, anti-viral agents, enzyme inhibitors, neurotoxins, opioids, hypnotics, anti-histamines, lubricants, tranquilizers, anti-convulsants, muscle relaxants, anti-Parkinson agents, anti-spasmodics and muscle contractants including channel blockers, miotics and anti-cholinergics, anti-glaucoma compounds, anti-parasite agents, anti-protozoal agents, and/or anti-fungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotics, targeting agents, chemotactic factors, receptors, neurotransmitters, proteins, cell response modifiers, cells, peptides, polynucleotides, viruses, and vaccines. In certain embodiments, the bioactive agent is a drug. In certain embodiments, the bioactive agent is a small molecule.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, the United States Pharmacopeia-25/National Formulary-20, published by the United States Pharmcopeial Convention, Inc., Rockville Md., 2001, and the "Pharmazeutische Wirkstoffe", edited by Von Keemann et al., Stuttgart/N.Y., 1987, all of which are incorporated herein by reference. Drugs for human use listed by the U.S. Food and Drug Administration (FDA) under 21 C.F.R. §§330.5, 331 through 361, and 440 through 460, and drugs for veterinary use listed by the FDA under 21 C.F.R. §§500 through 589, all of which are incorporated herein by reference, are also considered acceptable for use in accordance with the present invention.

The terms, "biodegradable", "bioerodable", or "resorbable" materials, as used herein, are intended to describe materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Biodegradable materials also include materials that are broken down within cells. Degradation may occur by hydrolysis, oxidation, enzymatic processes, phagocytosis, or other processes.

The term "biocompatible" as used herein, is intended to describe materials that, upon administration in vivo, do not induce undesirable side effects. In some embodiments, the material does not induce irreversible, undesirable side effects. In certain embodiments, a material is biocompatible if it does not induce long term undesirable side effects. In certain embodiments, the risks and benefits of administering a material are weighed in order to determine whether a material is sufficiently biocompatible to be administered to a subject.

The term "biomolecules" as used herein, refers to classes of molecules (e.g., proteins, amino acids, peptides, polynucleotides, nucleotides, carbohydrates, sugars, lipids, nucleoproteins, glycoproteins, lipoproteins, steroids, natural products, etc.) that are commonly found or produced in cells, whether the molecules themselves are naturally-occurring or artificially created (e.g., by synthetic or recombinant methods). For example, biomolecules include, but are not limited to, enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Exemplary growth factors include but are not limited to bone morphogenic proteins (BMP's) and their active fragments or subunits. In some embodiments, the biomolecule is a growth factor, chemotactic factor, cytokine, extracellular matrix molecule, or a fragment or derivative thereof, for example, a cell attachment sequence such as a peptide containing the sequence, RGD.

The term "carbohydrate" as used herein, refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2"-fluororibose, deoxyribose, and hexose). Carbohydrates may exist in many different forms, for example, conformers, cyclic forms, acyclic forms, stereoisomers, tautomers, anomers, and isomers.

The term "composite" as used herein, is used to refer to a unified combination of two or more distinct materials. The composite may be homogeneous or heterogeneous. For example, a composite may be a combination of bone particles and a polymer; or a combination of bone particles, polymers and antibiotics. In certain embodiments, the composite has a particular orientation.

The term "demineralized" is used herein to refer to bone (e.g., particles) that have been subjected to a process that causes a decrease in the original mineral content. As utilized herein, the phrase "superficially demineralized" as applied to bone particles refers to bone particles possessing at least about 90% by weight of their original inorganic mineral content. The phrase "partially demineralized" as applied to the bone particles refers to bone particles possessing from about 8% to about 90% by weight of their original inorganic mineral content, and the phrase "fully demineralized" as applied to the bone particles refers to bone particles possessing less than about 8% by weight, for example, less than about 1% by weight, of their original inorganic mineral content. The unmodified term "demineralized" as applied to the bone particles is intended to cover any one or combination of the foregoing types of demineralized bone particles.

The term "deorganified" as herein applied to matrices, particles, etc., refers to bone or cartilage matrices, particles, etc., that were subjected to a process that removes at least part of their original organic content. In some embodiments, at least 1%, 10%, 20%, 30%, 40%, 50%, 60%, 70%, 80%, 90%, or 99% of the organic content of the starting material is removed. Deorganified bone from which substantially all the organic components have been removed is termed "anorganic."

The term "flowable polymer material" as used herein, refers to a flowable composition including one or more of monomers, pre-polymers, oligomers, low molecular weight polymers, uncross-linked polymers, partially cross-linked polymers, partially polymerized polymers, polymers, or combinations thereof that have been rendered formable. One skilled in the art will recognize that a flowable polymer material need not be a polymer but may be polymerizable. In some embodiments, flowable polymer materials include polymers that have been heated past their glass transition or melting point. Alternatively or in addition, a flowable polymer material may include partially polymerized polymer, telechelic polymer, or prepolymer. A pre-polymer is a low molecular weight oligomer typically produced through step growth polymerization. The pre-polymer is formed with an excess of one of the components to produce molecules that are all terminated with the same group. For example, a diol and an excess of a diisocyanate may be polymerized to produce isocyanate terminated prepolymer that may be combined with a diol to form a polyurethane. Alternatively or in addition, a flowable polymer material may be a polymer material/solvent mixture that sets when the solvent is removed.

The term "mineralized" as used herein, refers to bone that has been subjected to a process that caused a decrease in their original organic content (e.g., de-fatting, de-greasing). Such a process can result in an increase in the relative inorganic mineral content of the bone. Mineralization may also refer to the mineralization of a matrix such as extracellular matrix or demineralized bone matrix. The mineralization process may take place either in vivo or in vitro.

The term "non-demineralized" as herein applied to bone or bone particles, refers to bone or bone-derived material (e.g., particles) that have not been subjected to a demineralization process (i.e., a procedure that totally or partially removes the original inorganic content of bone).

The term "nontoxic" is used herein to refer to substances which, upon ingestion, inhalation, or absorption through the skin by a human or animal, do not cause, either acutely or chronically, damage to living tissue, impairment of the central nervous system, severe illness or death.

The term "osteoconductive" as used herein, refers to the ability of a substance or material to provide surfaces which are receptive to the growth of new bone.

The term "osteogenic" as used herein, refers to the ability of a substance or material that can induce bone formation.

The term "osteoinductive" as used herein, refers to the quality of being able to recruit cells (e.g., osteoblasts) from the host that have the potential to stimulate new bone formation. In general, osteoinductive materials are capable of inducing heterotopic ossification, that is, bone formation in extraskeletal soft tissues (e.g., muscle).

The term "osteoimplant" is used herein in its broadest sense and is not intended to be limited to any particular shapes, sizes, configurations, compositions, or applications. Osteoimplant refers to any device or material for implantation that aids or augments bone formation or healing. Osteoimplants are often applied at a bone defect site, e.g., one resulting from injury, defect brought about during the course of surgery, infection, malignancy, inflammation, or developmental malformation. Osteoimplants can be used in a variety of orthopedic, neurosurgical, dental, and oral and maxillofacial surgical procedures such as the repair of simple and compound fractures and non-unions, external, and internal fixations, joint reconstructions such as arthrodesis, general arthroplasty, deficit filling, disectomy, laminectomy, anterior cerival and thoracic operations, spinal fusions, etc.

The terms "polynucleotide", "nucleic acid", or "oligonucleotide" as used herein, refer to a polymer of nucleotides. The terms "polynucleotide", "nucleic acid", and "oligonucleotide", may be used interchangeably. Typically, a polynucleotide comprises at least three nucleotides. DNAs and RNAs are exemplary polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thithymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose), or modified phosphate groups (e.g., phosphorothioates and 5'-N-phosphoramidite linkages). The polymer may also be a short strand of nucleic acids such as RNAi, siRNA, or shRNA.

The terms "polypeptide", "peptide", or "protein" as used herein, include a string of at least three amino acids linked together by peptide bonds. The terms "polypeptide", "peptide", and "protein", may be used interchangeably. In some embodiments, peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" or "oligosaccharide" as used herein, refer to any polymer or oligomer of carbohydrate residues. Polymers or oligomers may consist of anywhere from two to hundreds to thousands of sugar units or more. "Oligosaccharide" generally refers to a relatively low molecular weight polymer, while "polysaccharide" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly(dextrose), and fructose. In some embodiments, glycosaminoglycans are considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

The term "porogen" as used herein, refers to a chemical compound that may be part of the inventive composite and upon implantation/injection or prior to implantation/injection diffuses, dissolves, and/or degrades to leave a pore in the osteoimplant composite. A porogen may be introduced into the composite during manufacture, during preparation of the composite (e.g., in the operating room), or after implantation/injection. A porogen essentially reserves space in the composite while the composite is being molded but once the composite is implanted the porogen diffuses, dissolves, or degrades, thereby inducing porosity into the composite. In this way porogens provide latent pores. In certain embodiments, the porogen may be leached out of the composite before implantation/injection. This resulting porosity of the implant generated during manufacture or after implantation/injection (i.e., "latent porosity") is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars (e.g., sugar alcohols), polysaccharides (e.g., dextran (poly(dextrose)), water soluble small molecules, etc. Porogens can also be natural or synthetic polymers, oligomers, or monomers that are water soluble or degrade quickly under physiological conditions. Exemplary polymers include polyethylene glycol, poly(vinylpyrrollidone), pullulan, poly (glycolide), poly(lactide), poly(lactide-co-glycolide), other polyesters, and starches. In certain embodiments, bone particles utilized in provided composites or compositions may act as porogens. For example, osteoclasts resorb allograft and make pores in composites.

In some embodiments, porogens may refer to a blowing agent (i.e., an agent that participates in a chemical reaction to generate a gas). Water may act as such a blowing agent or porogen.

The term "porosity" as used herein, refers to the average amount of non-solid space contained in a material (e.g., a composite of the present invention). Such space is considered void of volume even if it contains a substance that is liquid at ambient or physiological temperature, e.g., 0.5° C. to 50° C. Porosity or void volume of a composite can be defined as the ratio of the total volume of the pores (i.e., void volume) in the material to the overall volume of composites. In some embodiments, porosity ($\epsilon$), defined as the volume fraction pores, can be calculated from composite foam density, which can be measured gravimetrically. Porosity may in certain embodiments refer to "latent porosity" wherein pores are only formed upon diffusion, dissolution, or degradation of a material occupying the pores. In such an instance, pores may be formed after implantation/injection. It will be appreciated by these of ordinary skill in the art that the porosity of a provided composite or composition may change over time, in some embodiments, after implantation/injection (e.g., after leaching of a porogen, when osteoclasts resorbing allograft bone, etc.). For the purpose of the present disclosure, implantation/injection may be considered to be "time zero" ($T_0$). In some embodiments, the present invention provides composites and/or compositions having a porosity of at least about 30%, at least about 40%, at least about 50%, at least about 60%, at least about 70%, at least about 80%, at least about 90% or more than 90%, at time zero. In certain embodiments, pre-molded composites and/or compositions may have a porosity of at least about 30%, at least about 40%, at least about 50%, at least about 60%, at least about 70%, at least about 80%, at least about 90% or more than 90%, at time zero. In certain embodiments, injectable composites and/or compositions may have a porosity of as low as 3% at time zero. In certain embodiments, injectable composites and/or compositions may cure in situ and have a porosity of at least about 30%, at least about 40%, at least about 50%, at least about 60%, at least about 70%, at least about 80%, at least about 90% or more than 90% after curing.

The term "remodeling" as used herein, describes the process by which native bone, processed bone allograft, whole bone sections employed as grafts, and/or other bony tissues are replaced with new cell-containing host bone tissue by the action of osteoclasts and osteoblasts. Remodeling also describes the process by which non-bony native tissue and tissue grafts are removed and replaced with new, cell-containing tissue in vivo. Remodeling also describes how inorganic materials (e.g., calcium-phosphate materials, such as β-tricalcium phosphate) is replaced with living bone.

The term "setting time" as used herein, is approximated by the tack-free time (TFT), which is defined as the time at which the material could be touched with a spatula with no adhesion of the spatula to the foam. At the TFT, the wound could be closed without altering the properties of the material.

The term "shaped" as used herein, is intended to characterize a material (e.g., composite) or an osteoimplant refers to a material or osteoimplant of a determined or regular form or configuration in contrast to an indeterminate or vague form or configuration (as in the case of a lump or other solid matrix of special form). Materials may be shaped into any shape, configuration, or size. For example, materials can be shaped as sheets, blocks, plates, disks, cones, pins, screws, tubes, teeth, bones, portions of bones, wedges, cylinders, threaded cylinders, and the like, as well as more complex geometric configurations.

The term "small molecule" as used herein, is used to refer to molecules, whether naturally-occurring or artificially created (e.g., via chemical synthesis), that have a relatively low molecular weight. In some embodiments, small molecules have a molecular weight of less than about 2,500 g/mol, for example, less than 1000 g/mol. In certain embodiments, small molecules are biologically active in that they produce a local or systemic effect in animals, such as mammals, e.g., humans. In certain embodiments, a small molecule is a drug. In certain embodiments, though not necessarily, a drug is one that has already been deemed safe and effective for use by an appropriate governmental agency or body (e.g., the U.S. Food and Drug Administration).

The term "transformation" as used herein, describes a process by which a material is removed from an implant site and replaced by host tissue after implantation. Transformation may be accomplished by a combination of processes, including but not limited to remodeling, degradation, resorption, and tissue growth and/or formation. Removal of the material may be cell-mediated or accomplished through chemical processes, such as dissolution and hydrolysis.

The term "wet compressive strength" as used herein, refers to the compressive strength of an osteoimplant after being immersed in physiological saline (e.g., phosphate-buffered saline (PBS), water containing 0.9 g NaCl/100 ml water, etc.) for a minimum of 12 hours (e.g., 24 hours). Compressive strength and modulus are well-known measurements of mechanical properties and is measured using the procedure described herein The term "working time" as used herein, is defined in the ISO9917 standard as "the period of time, measured from the start of mixing, during which it is possible to manipulate a dental material without an adverse effect on its properties" (Clarkin et al., *J Mater Sci: Mater Med* 2009; 20:1563-1570). In some embodiments, the working time for a two-component polyurethane is determined by the gel point, the time at which the crosslink density of the polymer network is sufficiently high that the material gels and no longer flows. According to the present invention, the working time is measured by loading the syringe with the reactive composite and injecting <0.25 ml every 30 s. The working time is noted as the time at which the material was more difficult to inject, indicating a significant change in viscosity.

DESCRIPTION OF DRAWING

FIG. 11 illustrates histological micrographs of Rabbit MBP/PUR composite plugs. In grayscale, old allograft is stained light gray, polymer is stained black, and cells are stained dark gray.

DETAILED DESCRIPTION OF CERTAIN EMBODIMENTS

Figure 1:
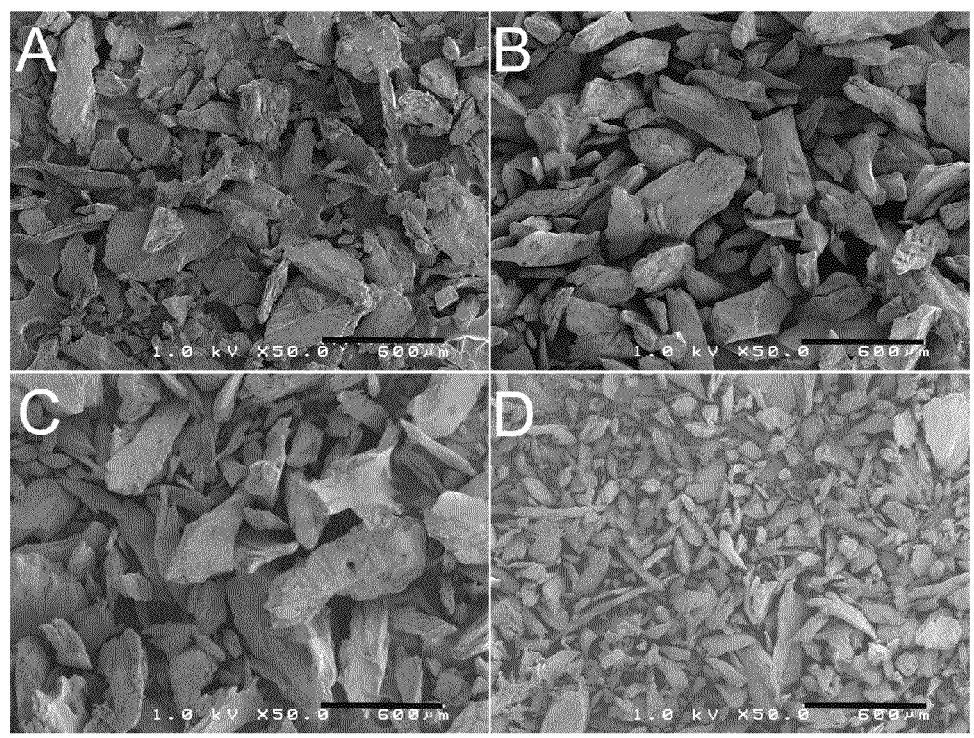
FIG. 1 illustrates SEM images of allograft bone particles: (a) B-MBP, (b) SDBP, (c) DFMBP, (d) H-SDBP.

As used herein and in the appended claims, the singular forms "a," "an" and "the" include plural references unless the content clearly dictates otherwise. All publications, patent applications, patents, and other references mentioned herein are incorporated by reference in their entirety.

Bone/polyurethane composites described herein include bone (e.g., bone particles), polyurethane, and in some embodiments, one or more additional components (e.g., a porogen and/or a bioactive agent). As described below, bone and biodegradable polyurethanes are combined to form a porous composite (e.g., an osteoimplant). In some embodiments, porous composites retain strength and/or release bioactive agents when present in a body. In some embodiments, composites degrade and are replaced by new tissue.

Inventive composites can be used in a large variety of clinical applications, for example, as bone void fillers, to repair or help healing of skeletal deficiencies resulting from trauma, tumors, surgery, iatrogenic, congenital, genetic, metabolic and degenerative or abnormal development, and inflammatory infection. In some embodiments, inventive composites promote cellular infiltration from adjacent osseous tissues, thus accelerating the remodeling process.

The invention also provides methods of preparing and using inventive composites as well as kits for preparing and/or administering inventive composites. Inventive porous composites may be prepared using any of a variety of methods. In some embodiments, inventive composites are prepared using a method that includes water as a blowing agent. In one embodiment, bone particles or other bone substitute materials are combined with polyurethanes and injected, extruded, molded, or similarly delivered to a tissue site (e.g., bony defect) of a subject. Inventive composites are engineered to set in situ to form a solid composite that may have a desired or predetermined mechanical strength. In certain embodiments, polyurethane present in a composition or composite may include monomers or pre-polymers. In some embodiments, polyurethane is a polymer that has been rendered formable through combination of two liquid components (i.e., a polyisocyanate prepolymer and a polyol).

Particulate Component

Particles used in accordance with the present invention may include a bone-derived material, an inorganic material, a bone substitute material, a composite material, or any combinations thereof.

Bone Particles.

Any kind of bone and/or bone-derived particles may be used in the present invention. In some embodiments, bone particles employed in the preparation of bone particle-containing composites are obtained from cortical, cancellous, and/or corticocancellous bone. Bone particles may be obtained from any vertebrate. Bone may be of autogenous, allogenic, and/or xenogeneic origin. In certain embodiments, bone particles are autogenous, that is, bone particles are from the subject being treated. In other embodiments, bone particles are allogenic (e.g., from donors). In certain embodiments, the source of bone may be matched to the eventual recipient of inventive composites (i.e., the donor and recipient are of the same species). For example, human bone particle is typically used in a human subject. In certain embodiments, bone particles are obtained from cortical bone of allogenic origin. In certain embodiments, bone particles are obtained from bone of xenogeneic origin. Porcine and bovine bone are types of xenogeneic bone tissue that can be used individually or in combination as sources for bone particles and may offer advantageous properties. Xenogenic bone tissue may be combined with allogenic or autogenous bone.

Bone particles can be formed by any process known to break down bone into small pieces. Exemplary processes for forming such particles include milling whole bone to produce fibers, chipping whole bone, cutting whole bone, grinding whole bone, fracturing whole bone in liquid nitrogen, or otherwise disintegrating the bone. Bone particles can optionally be sieved to produce particles of a specific size range. Bone particles may be of any shape or size. Exemplary shapes include spheroidal, plates, shards, fibers, cuboidal, sheets, rods, oval, strings, elongated particles, wedges, discs, rectangular, polyhedral, etc.

In some embodiments, bone particles have a medium or mean diameter about 1200 microns, 1100 microns, 1000 microns, 900 microns, 800 microns, 700 microns, 600 microns, 500 microns, 400 microns, 300 microns, 200 microns, 100 microns, etc. In some embodiments, diameters of bone particles are within a range between any of such sizes. For example, medium or mean diameters of bone particles have a range from approximately 100 microns to approximately 1000 microns.

As for irregularly shaped bone particles, recited dimension ranges may represent the length of the greatest or smallest dimension of the particle. As examples, bone particles can be pin shaped, with tapered ends having an average diameter of from about 100 microns to about 500 microns. As will be appreciated by one of skill in the art, for injectable composites, the maximum particle size will depend in part on the size of the cannula or needle through which the material will be delivered.

In some embodiments, particle size distribution of bone particles utilized in accordance with the present inventions with respect to a mean value or a median value may be plus or minus, e.g., about 10% or less of the mean value, about 20% or less of the mean value, about 30% or less of the mean value, about 40% or less of the mean value, about 50% or less of the mean value, about 60% or less of the mean value, about 70% or less of the mean value, about 80% or less of the mean value, or about 90% or less of the mean value.

In some embodiments, bone particles have a median or mean length of about 1200 microns, 1100 microns, 1000 microns, 900 microns, 800 microns, 700 microns, 600 microns, 500 microns, 400 microns, 300 microns, 200 microns, 100 microns, etc. In some embodiments, about 70, about 80 or about 90 percent of bone particles possess a median or mean length within a range of any of such sizes.

For bone particles that are fibers or other elongated particles, in some embodiments, at least about 90 percent of the particles possess a median or mean length in their greatest dimension in a range from approximately 100 microns to approximately 1000 microns. Particles may possess a median or mean length to median or mean thickness ratio from at least about 5:1 up to about 500:1, for example, from at least about 50:1 up to about 500:1, or from about 50:1 up to about 100:1; and a median or mean length to median or mean width ratio of from about 10:1 to about 200:1 and, for example, from about 50:1 to about 100:1. In certain embodiments, bone particles are short fibers having a cross-section of about 300 microns to about 100 microns and a length of about 0.1 mm to about 1 mm.

Processing of bone to provide particles may be adjusted to optimize for the desired size and/or distribution of bone particles. The properties of resulting inventive composites (e.g., mechanical properties) may also be engineered by adjusting weight percent, shapes, sizes, distribution, etc. of bone particles or other particles. For example, an inventive composite may be made more viscous and load bearing by including a higher percentage of particles.

U.S. Pat. Nos. 5,899,939; 5,507,813; 6,123,731; 6,294,041; 6,294,187; 6,332,779; 6,440,444; and 6,478,825; the contents of all of which are incorporated herein by reference, describe methods for preparing composites including allogenic bone for use in orthopedic applications.

Bone particles utilized in accordance with the present inventions may be demineralized, non-demineralized, mineralized, or anorganic. In some embodiments, bone particles are used "as is" in preparing inventive composites. In some embodiments, bone particles are defatted and disinfected. An exemplary defatting/disinfectant solution is an aqueous solution of ethanol. Other organic solvent may also be used in the defatting and disinfecting bone particles. For example, methanol, isopropanol, butanol, DMF, DMSO, diethyl ether, hexanes, glyme, tetrahydrofuran, chloroform, methylene chloride, and carbon tetrachloride may be used. In certain embodiments, a non-halogenated solvent is used. A defatting/disinfecant solution may also include a detergent (e.g., an aqueous solution of a detergent). Ordinarily, at least about 10 to about 40 percent by weight of water (i.e., about 60 to about 90 weight percent of defatting agent such as alcohol) should be present in the defatting/disinfecting solution to produce optimal lipid removal and disinfection within the shortest period of time. An exemplary concentration range of a defatting solution is from about 60 to about 85 weight percent alcohol, for example, about 70 weight percent alcohol.

In some embodiments, bone particles are demineralized. Bone particles can be optionally demineralized in accordance with known and/or conventional procedures in order to reduce their inorganic mineral content. Demineralization methods remove the inorganic mineral component of bone by employing acid solutions. Such methods are well known in the art, see for example, Reddi, et al., *Proc. Nat. Acad. Sci.*, 1972, 69:1601-1605, the contents of which are incorporated herein by reference. The strength of the acid solution, the shape and dimensions of the bone particles and the duration of the demineralization treatment will determine the extent of demineralization. Reference in this regard is made to Lewandrowski, et al., *J. Biomed. Mater. Res.*, 1996, 31:365-372 and U.S. Pat. No. 5,290,558, the contents of both of which are incorporated herein by reference.

In an exemplary defatting/disinfecting/demineralization procedure, bone particles are subjected to a defatting/disinfecting step, followed by an acid demineralization step. An exemplary defatting/disinfectant solution is an aqueous solution of ethanol. In some embodiments, at least about 10 to about 40 percent by weight of water (i.e., about 60 to about 90 weight percent of defatting agent such as alcohol) can be present in a defatting/disinfecting solution to produce optimal lipid removal and disinfection within a reasonable period of time. An exemplary concentration range of a defatting solution is from about 60 to about 85 weight percent alcohol, for example, about 70 weight percent alcohol. Ethanol is typically the alcohol used in this step; however, other alcohols such as methanol, propanol, isopropanol, denatured ethanol, etc. may also be used. Following defatting, bone particles can be immersed in acid over time to effect their demineralization. The acid also disinfects the bone by killing viruses, vegetative microorganisms, and spores. Acids which can be employed in this step include inorganic acids such as hydrochloric acid and organic acids such as peracetic acid. After acid treatment, demineralized bone particles can be rinsed with sterile water to remove residual amounts of acid and thereby raise the pH. Bone particles may be dried, for example, by lyophilization, before being incorporated into a composite. Bone particles may be stored under aseptic conditions, for example, in a lyophilized state, until they are used or sterilized using known methods (e.g., gamma irradiation) shortly before combining them with polyurethanes used in inventive composites.

As utilized herein, the phrase "superficially demineralized" as applied to the bone particles refers to bone particles possessing at least about 90% by weight of their original inorganic mineral content. The phrase "partially demineralized" as applied to the bone particles refers to bone particles possessing from about 8% to about 90% weight of their original inorganic mineral content, and the phrase "fully demineralized" as applied to the bone particles refers to bone particles possessing less than about 8%, preferably less than about 1%, by weight of their original inorganic mineral content. The unmodified term "demineralized" as applied to the bone particles is intended to cover any one or combination of the foregoing types of demineralized bone particles, that is, superficially demineralized, partially demineralized, or fully demineralized bone particles.

In alternative embodiments, surfaces of bone particles may be lightly demineralized according to the procedures in our commonly owned U.S. patent application, U.S. Ser. No. 10/285,715, filed Nov. 1, 2002, published as U.S. Patent Publication No. 2003/0144743, on Jul. 31, 2003, the contents of which are incorporated herein by reference. Even minimal demineralization, for example, of less than 5% removal of the inorganic phase, increases the hydroxylation of bone fibers and the surface concentration of amine groups. Demineralization may be so minimal, for example, less than 1%, that the removal of the calcium phosphate phase is almost undetectable. Rather, the enhanced surface concentration of reactive groups defines the extent of demineralization. This may be measured, for example, by titrating the reactive groups. Surface composition can also be measured by x-ray photoelectron spectroscopy (XPS), an experimental technique that measures the atomic composition of the top 1-10 nm of the surface. In some embodiments, in a polymerization reaction that utilizes the exposed allograft surfaces to initiate a reaction, the amount of unreacted monomer remaining may be used to estimate reactivity of the surfaces. Surface reactivity may be assessed by a surrogate mechanical test, such as a peel test of a treated coupon of bone adhering to a polymer.

In certain embodiments, bone particles are subjected to a process that partially or totally removes their initial organic content to yield mineralized and anorganic bone particles, respectively. Different mineralization methods have been developed and are known in the are (Hurley, et al., *Milit. Med.* 1957, 101-104; Kershaw, *Pharm. J.* 6:537, 1963; and U.S. Pat. No. 4,882,149; each of which is incorporated herein by reference). For example, a mineralization procedure can include a de-greasing step followed by a basic treatment (with ammonia or another amine) to degrade residual proteins and a water washing (U.S. Pat. Nos. 5,417,975 and 5,573,771; both of which are incorporated herein by reference). Another example of a mineralization procedure includes a defatting step where bone particles are sonicated in 70% ethanol for 1-3 hours.

In some embodiments, bone particles can be modified in one or more ways, e.g., their protein content can be augmented or modified as described, for example, in U.S. Pat. Nos. 4,743,259 and 4,902,296, the contents of both of which are incorporated herein by reference.

Mixtures or combinations of one or more of the foregoing types of bone particles can be employed. For example, one or more of the foregoing types of demineralized bone particles can be employed in combination with non-demineralized bone particles, i.e., bone particles that have not been subjected to a demineralization process, or inorganic materials. The amount of each individual type of bone particle employed can vary widely depending on the mechanical and biological properties desired. Thus, in some embodiments, mixtures of bone particles of various shapes, sizes, and/or degrees of demineralization may be assembled based on the desired mechanical, thermal, chemical, and biological properties of a composite. A desired balance between the various properties of composites (e.g., a balance between mechanical and biological properties) may be achieved by using different combinations of particles. Suitable amounts of various particle types can be readily determined by those skilled in the art on a case-by-case basis by routine experimentation.

The differential in strength, osteogenicity, and other properties between partially and fully demineralized bone particles on the one hand, and non-demineralized, superficially demineralized bone particles, inorganic ceramics, and other bone substitutes on the other hand can be exploited. For example, in order to increase the compressive strength of an osteoimplant, the ratio of nondemineralized and/or superficially demineralized bone particles to partially or fully demineralized bone particles may favor the former, and vice versa. Bone particles in composites also play a biological role. Non-demineralized bone particles bring about new bone in-growth by osteoconduction. Demineralized bone particles likewise play a biological role in bringing about new bone in-growth by osteoinduction. Both types of bone particles are gradually remodeled and replaced by new host bone as degradation of the composite progresses over time. Thus, the use of various types of bone particles can be used to control the overall mechanical and biological properties, (e.g., strength, osteoconductivity, and/or osteoinductivity, etc.) of osteoimplants.

Surface Modification.

Bone particles utilized in accordance with the present invention may be optionally treated to enhance their interaction with polyurethanes and/or to confer some properties to particle surface. While some bone particles will interact readily with monomers and be covalently linked to polyurethane matrices, it may be desirable to modify surface of bone particles to facilitate their incorporation into polymers that do not bond well to bone, such as poly(lactides). Surface modification may provide a chemical substance that is strongly bonded to the surface of bone, e.g., covalently bonded to the surface. Bone particles may, alternatively or additionally, be coated with a material to facilitate interaction with polymers of inventive composites.

In some embodiments, silane coupling agents are employed to link a monomer or initiator molecule to the surface of bone particles. Silane has at least two sections, a set of leaving groups and at least an active group. An active group may be connected to the silicon atom in the silane by an elongated tether group. An exemplary silane coupling agent is 3-trimethoxysilylpropylmethacrylate, available from Union Carbide. Three methoxy groups are leaving groups, and the methacrylate active group is connected to the silicon atom by a propyl tether group. In some embodiments, a leaving group is an alkoxy group such as methoxy or ethoxy. Depending on the solvent used to link the coupling agent to bone particles, hydrogen or alkyl groups such as methyl or ethyl may serve as leaving groups. The length of tethers determines the intimacy of connection between polymers and bone particles. By providing a spacer between bone particles and active groups, the tether also reduces competition between chemical groups at the particle surface and the active group and makes the active group more accessible to monomers during polymerization.

In some embodiments, an active group is an analog of monomers of a polymer used in inventive composites. For example, amine active groups will be incorporated into polyurethane matrices, copolymers (e.g., polyesters, polycarbonates, polycaprolactone), and other polymer classes based on monomers that react with amines, even if the polymer does not contain an amine. Hydroxy-terminated silanes will be incorporated into polyamino acids, polyesters, polycaprolactone, polycarbonates, polyurethanes, and other polymer classes that include hydroxylated monomers. Aromatic active groups or active groups with double bonds will be incorporated into vinyl polymers and other polymers that grow by radical polymerization (e.g., polyacrylates, polymethacrylates). It is not necessary that the active group be monofunctional. Indeed, it may be preferable that active groups that are to be incorporated into polymers via step polymerization be difunctional. A silane having two amines, even if one is a secondary amine, will not terminate a polymer chain but can react with ends of two different polymer chains. Alternatively, the active group may be branched to provide two reactive groups in the primary position.

An exemplary list of silanes that may be used with the present invention is provided in U.S. Patent Publication No. 2004/0146543, the contents of which are incorporated herein by reference. Silanes are available from companies such as Union Carbide, AP Resources Co. (Seoul, South Korea), and BASF. Where a silane contains a potentially non-biocompatible moiety as the active group, it may be used to tether a biocompatible compound to bone particles using a reaction in which the non-biocompatible moiety is a leaving group. It may be desirable to attach the biocompatible compound to the silane before attaching the silane to the bone particle, regardless of whether the silane is biocompatible or not. The derivatized silanes may be mixed with silanes that can be incorporated directly into the polymer and reacted with bone particles, coating the bone particles with a mixture of "bioactive" silanes and "monomer" silanes. U.S. Pat. No. 6,399,693, the contents of which are incorporated herein by reference discloses composites of silane modified polyaromatic polymers and bone. In some embodiments, silane-derivatized polymers may be used in inventive composites instead of or in addition to first silanizing bone particles. In certain embodiments, polyurethanes and any copolymers used in accordance with the present inventions may not include silane modified polyaromatic polymers.

The active group of silanes may be incorporated directly into polymers or may be used to attach a second chemical group to bone particles. For example, if a particular monomer polymerizes through a functional group that is not commercially available as a silane, the monomer may be attached to the active group.

Non-silane linkers may also be employed to produce composites according to the invention. For example, isocyanates will form covalent bonds with hydroxyl groups on the surface of hydroxyapatite ceramics (de Wijn, et al., *Fifth World Biomaterials Congress*, May 29-Jun. 2, 1996, Toronto, CA). Isocyanate anchors, with tethers and active groups similar to those described with respect to silanes, may be used to attach monomer-analogs to bone particles or to attach chemical groups that will link covalently or non-covalently with a polymer side group. Polyamines, organic compounds containing one or more primary, secondary, or tertiary amines, will also bind with both the bone particle surface and many monomer and polymer side groups. Polyamines and isocyanates may be obtained from Aldrich.

Alternatively or additionally, biologically active compounds such as a biomolecule, a small molecule, or a bioactive agent may be attached to bone particles through a linker. For example, mercaptosilanes will react with sulfur atoms in proteins to attach them to bone particles. Aminated, hydroxylated, and carboxylated silanes will react with a wide variety of functional groups. Of course, the linker may be optimized for the compound being attached to bone particles.

Biologically active molecules can modify non-mechanical properties of inventive composites as they degrade. For example, immobilization of a drug on bone particles allows it to be gradually released at an implant site as the composite degrades. Anti-inflammatory agents embedded within inventive composites will control inflammatory response long after an initial response to injection of the composites. For example, if a piece of the composite fractures several weeks after injection, immobilized compounds will reduce the intensity of any inflammatory response, and the composite will continue to degrade through hydrolytic or physiological processes. In some embodiments, compounds may also be immobilized on the bone particles that are designed to elicit a particular metabolic response or to attract cells to injection sites.

Some biomolecules, small molecules, and bioactive agents may also be incorporated into polyurethane matrices used in inventive composites. For example, many amino acids have reactive side chains. The phenol group on tyrosine has been exploited to form polycarbonates, polyarylates, and polyiminocarbonates (see Pulapura, et al., *Biopolymers*, 1992, 32: 411-417; and Hooper, et al., *J. Bioactive and Compatible Polymers*, 1995, 10:327-340, the entire contents of both of which are incorporated herein by reference). Amino acids such as lysine, arginine, hydroxylysine, proline, and hydroxyproline also have reactive groups and are essentially trifunctional. Amino acids such as valine, which has an isopropyl side chain, are still difunctional. Such amino acids may be attached to the silane and still leave one or two active groups available for incorporation into a polymer.

Non-biologically active materials may also be attached to bone particles. For example, radiopaque (e.g., barium sulfate), luminescent (e.g., quantum dots), or magnetically active particles (e.g., iron oxide) may be attached to bone particles using the techniques described above. Mineralized bone particles are an inherently radiopaque component of some embodiments of present inventions, whereas demineralized bone particles, another optional component of inventive composites, are not radiopaque. To enhance radiopacity of inventive composites, mineralized bone particles can be used. Another way to render radiopaque the polymers utilized in accordance with the present inventions, is to chemically modify them such that a halogen (e.g., iodine) is chemically incorporated into the polyurethane matrices, as in U.S. patent application Ser. No. 10/952,202, now published as U.S. Patent Publication No. 2006-0034769, whose content is incorporated herein by reference.

If a material, for example, a metal atom or cluster, cannot be produced as a silane or other group that reacts with bone particles, then a chelating agent may be immobilized on bone particle surface and allowed to form a chelate with the atom or cluster. As bone particles and polymers used in the present invention are resorbed, these non-biodegradable materials may be removed from tissue sites by natural metabolic processes, allowing degradation of the polymers and resorption of the bone particles to be tracked using standard medical diagnostic techniques.

In some embodiments, bone particle surface is chemically treated before being mixed with polyurethane. For example, non-demineralized bone particles may be rinsed with phosphoric acid, e.g., for 1 to 15 minutes in a 5-50% solution by volume. Those skilled in the art will recognize that the relative volume of bone particles and phosphoric acid solution (or any other solution used to treat bone particles), may be optimized depending on the desired level of surface treatment. Agitation will also increase the uniformity of the treatment both along individual particles and across an entire sample of particles. A phosphoric acid solution reacts with mineral components of bone particles to coat the bone particles with calcium phosphate, which may increase the affinity of the surface for inorganic coupling agents such as silanes and for polymer components of the composite. As noted above, bone particle surface may be partially demineralized to expose the collagen fibers.

Collagen fibers exposed by demineralization are typically relatively inert but have some exposed amino acid residues that can participate in reactions. Collagen may be rendered more reactive by fraying triple helical structures of the collagen to increase exposed surface area and number of exposed amino acid residues. This not only increases surface area of bone particles available for chemical reactions but also for their mechanical interactions with polymers as well. Rinsing partially demineralized bone particles in an alkaline solution will fray collagen fibrils. For example, bone particles may be suspended in water at a pH of about 10 for about 8 hours, after which the solution is neutralized. One skilled in the art will recognize that this time period may be increased or decreased to adjust the extent of fraying. Agitation, for example, in an ultrasonic bath, may reduce the processing time. Alternatively or additionally, bone particles may be sonicated with water, surfactant, alcohol, or some combination of these.

In some embodiments, collagen fibers at bone particle surface may be cross-linked. A variety of cross-linking techniques suitable for medical applications are well known in the art (see, for example, U.S. Pat. No. 6,123,781, the contents of which are incorporated herein by reference). For example, compounds like 1-ethyl-3-(3-dimethylaminopropyl) carbodiimide hydrochloride, either alone or in combination with N-hydroxysuccinimide (NHS) will crosslink collagen at physiologic or slightly acidic pH (e.g., in pH 5.4 MES buffer). Acyl azides and genipin, a naturally occurring bicyclic compound including both carboxylate and hydroxyl groups, may also be used to cross-link collagen chains (see Simmons, et al, *Biotechnol. Appl. Biochem.*, 1993, 17:23-29; PCT Publication WO98/19718, the contents of both of which are incorporated herein by reference). Alternatively or additionally, hydroxymethyl phosphine groups on collagen may be reacted with the primary and secondary amines on neighboring chains (see U.S. Pat. No. 5,948,386, the entire contents of which are incorporated herein by reference). Standard cross-linking agents such as mono- and dialdehydes, polyepoxy compounds, tanning agents including polyvalent metallic oxides, organic tannins, and other plant derived phenolic oxides, chemicals for esterification or carboxyl groups followed by reaction with hydrazide to form activated acyl azide groups, dicyclohexyl carbodiimide and its derivatives and other heterobifunctional crosslinking agents, hexamethylene diisocyanate, and sugars may also be used to cross-link collagens. Bone particles are then washed to remove all leachable traces of materials. In other embodiments, enzymatic cross-linking agents may be used. Additional cross-linking methods include chemical reaction, irradiation, application of heat, dehydrothermal treatment, enzymatic treatment, etc. One skilled in the art will easily be able to determine the optimal concentrations of cross-linking agents and incubation times for the desired degree of cross-linking.

Both frayed and unfrayed collagen fibers may be derivatized with monomer, pre-polymer, oligomer, polymer, initiator, and/or biologically active or inactive compounds, including but not limited to biomolecules, bioactive agents, small molecules, inorganic materials, minerals, through reactive amino acids on the collagen fiber such as lysine, arginine, hydroxylysine, proline, and hydroxyproline. Monomers that link via step polymerization may react with these amino acids via the same reactions through which they polymerize. Vinyl monomers and other monomers that polymerize by chain polymerization may react with these amino acids via their reactive pendant groups, leaving the vinyl group free to polymerize. Alternatively, or in addition, bone particles may be treated to induce calcium phosphate deposition and crystal formation on exposed collagen fibers. Calcium ions may be chelated by chemical moieties of the collagen fibers, and/or calcium ions may bind to the surface of the collagen fibers. James et al., *Biomaterials* 20:2203-2313, 1999; incorporated herein by reference. The calcium ions bound to the collagen provides a biocompatible surface, which allows for the attachment of cells as well as crystal growth. The polymer will interact with these fibers, increasing interfacial area and improving the wet strength of the composite.

In some embodiments, the surface treatments described above or treatments such as etching may be used to increase the surface area or surface roughness of bone particles. Such treatments increase the interfacial strength of the particle/polymer interface by increasing the surface area of the interface and/or the mechanical interlocking of bone particles and polyurethane. Such surface treatments may also be employed to round the shape or smooth the edges of bone particles to facilitate delivery of the inventive composite. Such treatment is particularly useful for injectable composites.

In some embodiments, surface treatments of bone particles are optimized to enhance covalent attractions between bone particles and polyurethanes. In some embodiments, the surface treatment may be designed to enhance non-covalent interactions between bone particle and polyurethane matrix. Exemplary non-covalent interactions include electrostatic interactions, hydrogen bonding, pi-bond interactions, hydrophobic interactions, van der Waals interactions, and mechanical interlocking. For example, if a protein or a polysaccharide is immobilized on bone particle, the chains of polymer matrix will become physically entangled with long chains of the biological macromolecules when they are combined. Charged phosphate sites on the surface of bone particles, produced by washing the bone particles in basic solution, will interact with the amino groups present in many biocompatible polymers, especially those based on amino acids. The pi-orbitals on aromatic groups immobilized on a bone particle will interact with double bonds and aromatic groups of the polymer.

Additional Particulate Materials.

Any type of additional components comprising inorganic materials and/or other bone substitute materials (i.e., compositions similar to natural bone such as collagen, biocompatible polymers, osteoinductive agents, other commercial bone graft products, any composite graft, etc.), may be utilized in the present invention. Inorganic materials, including but not limited to, calcium phosphate materials, and other bone substitute materials, may also be exploited for use as particulate inclusions in the inventive composites. Exemplary materials utilized in accordance with the present invention include aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, and BIOGLASS™, a calcium phosphate silica glass available from U.S. Biomaterials Corporation. Substituted calcium phosphate phases are also contemplated for use with the invention, including but not limited to fluorapatite, chlorapatite, magnesium-substituted tricalcium phosphate, and carbonate hydroxyapatite. In certain embodiments, the inorganic material is a substituted form of hydroxyapatite. For example, hydroxyapatite may be substituted with other ions such as fluoride, chloride, magnesium, sodium, potassium, and groups such as silicates, silicon dioxides, carbonates, etc. Additional calcium phosphate phases suitable for use with the invention include those disclosed in U.S. Pat. Nos. RE 33,161 and RE 33,221 to Brown et al.; U.S. Pat. Nos. 4,880,610; 5,034,059; 5,047,031; 5,053,212; 5,129,905; 5,336,264; and 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat. Nos. 5,717,006 and 6,001,394 to Daculsi et al., U.S. Pat. No. 5,605,713 to Boltong et al., U.S. Pat. No. 5,650,176 to Lee et al., and U.S. Pat. No. 6,206,957 to Driessens et al, and biologically-derived or biomimetic materials such as those identified in Lowenstam H A, Weiner S, *On Biomineralization*, Oxford University Press, 1989; each of which is incorporated herein by reference.

In some embodiments, a particulate composite material may be employed to combine with inventive composites in the present invention. For example, inorganic materials such as those described above may be combined with proteins such as bovine serum albumin (BSA), collagen, or other extracellular matrix components to form a composite. In some embodiments, inorganic materials or bone-derived materials may be combined with synthetic or natural polymers to form a composite using the techniques described in our co-pending U.S. patent applications, U.S. Ser. No. 10/735,135, filed Dec. 12, 2003; U.S. Ser. No. 10/681,651, filed Oct. 8, 2003; and U.S. Ser. No. 10/639,912, filed Aug. 12, 2003, the contents of all of which are incorporated herein by reference.

Polymer Component

Synthetic polymers can be designed with properties targeted for a given clinical application. According to the present invention, polyurethanes (PUR) are a useful class of biomaterials due to the fact that they can be injectable or moldable as a reactive liquid that subsequently cures to form a porous composite. These materials also have tunable degradation rates, which are shown to be highly dependent on the choice of polyol and isocyanate components (Hafeman et al., *Pharmaceutical Research* 2008; 25(10):2387-99; Storey et al., *J Poly Sci Pt A: Poly Chem* 1994; 32:2345-63; Skarja et al., *J App Poly Sci* 2000; 75:1522-34). Polyurethanes have tunable mechanical properties, which can also be enhanced with the addition of bone particles and/or other components (Adhikari et al., *Biomaterials* 2008; 29:3762-70; Goma et al., *J Biomed Mater Res Pt A* 2003; 67A(3):813-27) and exhibit elastomeric rather than brittle mechanical properties.

Polyurethanes can be made by reacting together the components of a two-component composition, one of which includes a polyisocyanate while the other includes a component having two or more hydroxyl groups (i.e., polyols) to react with the polyisocyanate. For example, U.S. Pat. No. 6,306,177, discloses a method for repairing a tissue site using polyurethanes, the content of which is incorporated by reference.

It is to be understood that by "a two-component composition" it means a composition comprising two essential types of polymer components. In some embodiments, such a composition may additionally comprise one or more other optional components.

In some embodiments, polyurethane is a polymer that has been rendered formable through combination of two liquid components (i.e., a polyisocyanate prepolymer and a polyol). In some embodiments, a polyisocyanate prepolymer or a polyol may be a molecule with two or three isocyanate or hydroxyl groups respectively. In some embodiments, a polyisocyanate prepolymer or a polyol may have at least four isocyanate or hydroxyl groups respectively.

Synthesis of porous polyurethane results from a balance of two simultaneous reactions. Reactions, in some embodiments, are illustrated below in Scheme 1. One is a gelling reaction, where an isocyanates and a polyester polyol react to form urethane bonds. The one is a blowing reaction. An isocyanate can react with water to form carbon dioxide gas, which acts as a lowing agent to form pores of polyurethane foam. The relative rates of these reactions determine the scaffold morphology, working time, and setting time.

Exemplary gelling and blowing reactions in forming of polyurethane are shown in Scheme 1 below, where $R_1$, $R_2$ and $R_3$, for example, can be oligomers of caprolactone, lactide and glycolide respectively.

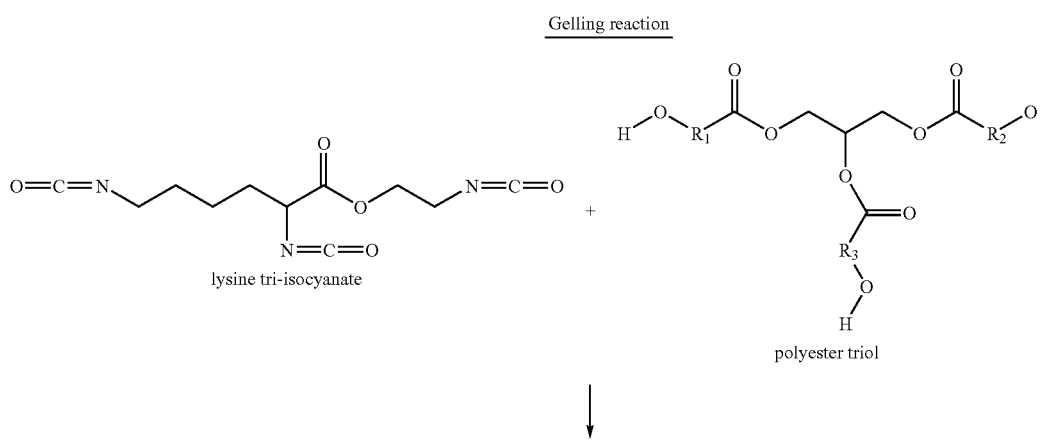

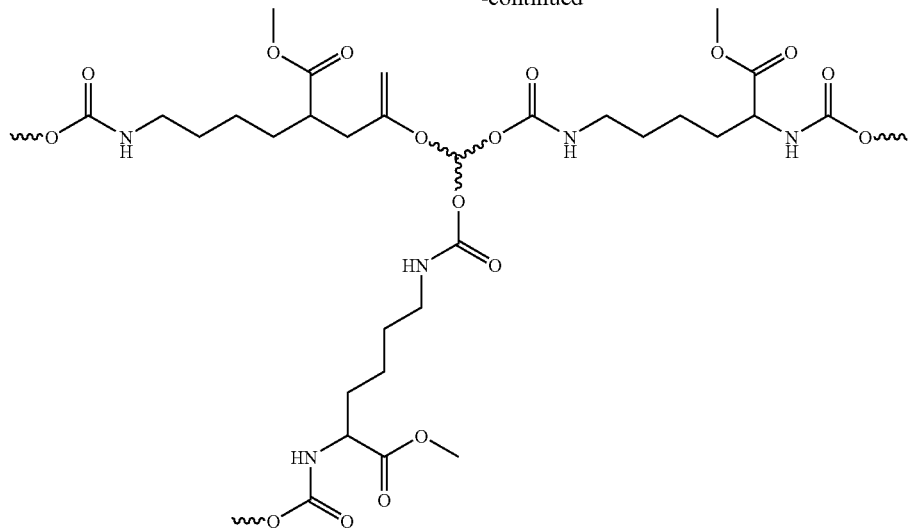

Blowing reaction

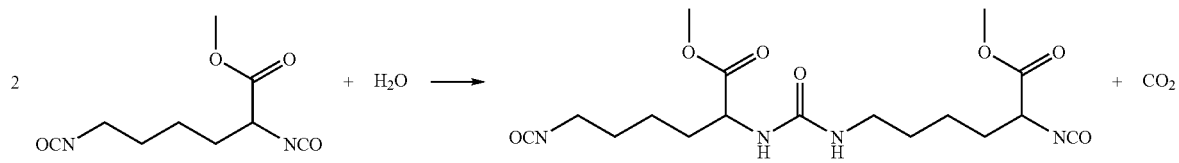

Biodegradable polyurethane scaffolds synthesized from aliphatic polyisocyanates been shown to degrade into non-toxic compounds and support cell attachment and proliferation in vitro. A variety of polyurethane polymers suitable for use in the present invention are known in the art, many of which are listed in commonly owned applications: U.S. Ser. No. 10/759,904 filed on Jan. 16, 2004, entitled "Biodegradable polyurethanes and use thereof" and published under No. 2005-0013793; U.S. Ser. No. 11/667,090 filed on Nov. 5, 2005, entitled "Degradable polyurethane foams" and published under No. 2007-0299151; U.S. Ser. No. 12/298,158 filed on Apr. 24, 2006, entitled "Biodegradable polyurethanes" and published under No. 2009-0221784; all of which are incorporated herein by reference. Polyurethanes described in U.S. Ser. No. 11/336,127 filed on Jan. 19, 2006 and published under No. 2006-0216323, which is entitled "Polyurethanes for Osteoimplants" and incorporated herein by reference, may be used in some embodiments of the present invention.

Polyurethanes foams may be prepared by contacting an isocyanate-terminated prepolymer (component 1, e.g, polyisocyanate prepolymer) with a hardener (component 2) that includes at least a polyol (e.g., a polyester polyol) and water, a catalyst and optionally, a stabilizer, a porogen, PEG, etc. In some embodiments, multiple polyurethanes (e.g., different structures, difference molecular weights) may be used in a composite/composition of the present invention. In some embodiments, other biocompatible and/or biodegradable polymers may be used with polyurethanes in accordance with the present invention. In some embodiments, biocompatible co-polymers and/or polymer blends of any combination thereof may be exploited.

Polyurethanes used in accordance with the present invention can be adjusted to produce polymers having various physiochemical properties and morphologies including, for example, flexible foams, rigid foams, elastomers, coatings, adhesives, and sealants. The properties of polyurethanes are controlled by choice of the raw materials and their relative concentrations. For example, thermoplastic elastomers are characterized by a low degree of cross-linking and are typically segmented polymers, consisting of alternating hard (diisocyanates and chain extenders) and soft (polyols) segments. Thermoplastic elastomers are formed from the reaction of diisocyanates with long-chain diols and short-chain diol or diamine chain extenders. In some embodiments, pores in bone/polyurethanes composites in the present invention are interconnected and have a diameter ranging from approximately 50 to approximately 1000 microns.

Prepolymer.

Polyurethane prepolymers can be prepared by contacting a polyol with an excess (typically a large excess) of a polyisocyanate. The resulting prepolymer intermediate includes an adduct of polyisocyanates and polyols solubilized in an excess of polyisocyanates. Prepolymer can, in some embodiments, be formed by using an approximately stoichiometric amount of polyisocyanates in forming a prepolymer and subsequently adding additional polyisocyanates. The prepolymer therefore exhibits both low viscosity, which facilitates processing, and improved miscibility as a result of the polyisocyanate-polyol adduct. Polyurethane networks can, for example, then be prepared by reactive liquid molding, wherein the prepolymer is contacted with a polyester polyol to form a reactive liquid mixture (i.e., a two-component composition) which is then cast into a mold and cured.

Polyisocyanates or multi-isocyanate compounds for use in the present invention include aliphatic polyisocyanates. Exemplary aliphatic polyisocyanates include, but are not limited to, lysine diisocyanate, an alkyl ester of lysine diisocyanate (for example, the methyl ester or the ethyl ester), lysine triisocyanate, hexamethylene diisocyanate, isophorone diisocyanate (IPDI), 4,4'-dicyclohexylmethane diisocyanate ($H_{12}MDI$), cyclohexyl diisocyanate, 2,2,4-(2,2,4)-trimethylhexamethylene diisocyanate (TMDI), dimers prepared form aliphatic polyisocyanates, trimers prepared from aliphatic polyisocyanates and/or mixtures thereof. In some embodiments, hexamethylene diisocyanate (HDI) trimer sold as Desmodur N3300A may be a polyisocyanate utilized in the present invention. In some embodiments, polyisocyanates used in the present invention includes approximately 10 to 55% NCO by weight (wt % NCO=100*(42/Mw)). In some embodiments, polyisocyanates include approximately 15 to 50% NCO.

Polyisocyanate prepolymers provide an additional degree of control over the structure of biodegradable polyurethanes. Prepared by reacting polyols with isocyanates, NCO-terminated prepolymers are oligomeric intermediates with isocyanate functionality as shown in Scheme 1. To increase reaction rates, urethane catalysts (e.g., tertiary amines) and/or elevated temperatures (60-90° C.) may be used (see, Guelcher, *Tissue Engineering: Part B*, 14 (1) 2008, pp 3-17).

Polyols used to react with polyisocyanates in preparation of NCO-terminated prepolymers refer to molecules having at least two functional groups to react with isocyanate groups. In some embodiments, polyols have a molecular weight of no more than 1000 g/mol. In some embodiments, polyols have a rang of molecular weight between about 100 g/mol to about 500 g/mol. In some embodiments, polyols have a rang of molecular weight between about 200 g/mol to about 400 g/mol. In certain embodiments, polyols (e.g., PEG) have a molecular weight of about 200 g/mol. Exemplary polyols include, but are not limited to, PEG, glycerol, pentaerythritol, dipentaerythritol, tripentaerythritol, 1,2,4-butanetriol, trimethylolpropane, 1,2,3-trihydroxyhexane, myo-inositol, ascorbic acid, a saccharide, or sugar alcohols (e.g., mannitol, xylitol, sorbitol etc.). In some embodiments, polyols may comprise multiple chemical entities having reactive hydrogen functional groups (e.g., hydroxy groups, primary amine groups and/or secondary amine groups) to react with the isocyanate functionality of polyisocyanates.

In some embodiments, polyisocyanate prepolymers are resorbable. Zhang and coworkers synthesized biodegradable lysine diisocyanate ethyl ester (LDI)/glucose polyurethane foams proposed for tissue engineering applications. In those studies, NCO-terminated prepolymers were prepared from LDI and glucose. The prepolymers were chain-extended with water to yield biocompatible foams which supported the growth of rabbit bone marrow stromal cells in vitro and were non-immunogenic in vivo. (see Zhang, et al., *Biomaterials* 21: 1247-1258 (2000), and Zhang, et al., *Tiss. Eng.*, 8(5): 771-785 (2002), both of which are incorporated herein by reference).

In some embodiments, prepared polyisocyanate prepolymer can be a flowable liquid at processing conditions. In general, the processing temperature is no greater than 60° C. In some embodiments, the processing temperature is ambient temperature (25° C.).

Polyols.

Polyols utilized in accordance with the present invention can be amine- and/or hydroxyl-terminated compounds and include, but are not limited to, polyether polyols (such as polyethylene glycol (PEG or PEO), polytetramethylene etherglycol (PTMEG), polypropylene oxide glycol (PPO)); amine-terminated polyethers; polyester polyols (such as polybutylene adipate, caprolactone polyesters, castor oil); and polycarbonates (such as poly(1,6-hexanediol) carbonate). In some embodiments, polyols may be (1) molecules having multiple hydroxyl or amine functionality, such as glucose, polysaccharides, and castor oil; and (2) molecules (such as fatty acids, triglycerides, and phospholipids) that have been hydroxylated by known chemical synthesis techniques to yield polyols.

Polyols used in the present invention may be polyester polyols. In some embodiments, polyester polyols may include polyalkylene glycol esters or polyesters prepared from cyclic esters. In some embodiments, polyester polyols may include poly(ethylene adipate), poly(ethylene glutarate), poly(ethylene azelate), poly(trimethylene glutarate), poly (pentamethylene glutarate), poly(diethylene glutarate), poly (diethylene adipate), poly(triethylene adipate), poly(1,2-propylene adipate), mixtures thereof, and/or copolymers thereof. In some embodiments, polyester polyols can include, polyesters prepared from caprolactone, glycolide, D, L-lactide, mixtures thereof, and/or copolymers thereof. In some embodiments, polyester polyols can, for example, include polyesters prepared from castor-oil. When polyurethanes degrade, their degradation products can be the polyols from which they were prepared from.

In some embodiments, polyester polyols can be miscible with prepared prepolymers used in reactive liquid mixtures (i.e., two-component composition) of the present invention. In some embodiments, surfactants or other additives may be included in the reactive liquid mixtures to help homogenous mixing.

The glass transition temperature (Tg) of polyester polyols used in the reactive liquids to form polyurethanes can be less than 60° C., less than 37° C. (approximately human body temperature) or even less than 25° C. In addition to affecting flowability at processing conditions, Tg can also affect degradation. In general, a Tg of greater than approximately 37° C. will result in slower degradation within the body, while a Tg below approximately 37° C. will result in faster degradation.

Molecular weight of polyester polyols used in the reactive liquids to form polyurethanes can, for example, be adjusted to control the mechanical properties of polyurethanes utilized in accordance with the present invention. In that regard, using polyester polyols of higher molecular weight results in greater compliance or elasticity. In some embodiments, polyester polyols used in the reactive liquids may have a molecular weight less than approximately 3000 Da. In certain embodiments, the molecular weight may be in the range of approximately 200 to 2500 Da or 300 to 2000 Da. In some embodiments, the molecular weight may be approximately in the range of approximately 450 to 1800 Da or 450 to 1200 Da.

In some embodiments, a polyester polyol comprise poly (caprolactone-co-lactide-co-glycolide), which has a molecular weight in a range of 200 Da to 2500 Da, or 300 Da to 2000 Da.

In some embodiments, polyols may include multiply types of polyols with different structures, molecular weight, properties, etc.

Additional Components.

In accordance with the present invention, two-component compositions (i.e., polyprepolymers and polyols) to form porous composites may be used with other agents and/or catalysts. Zhang et al. have found that water may be an adequate blowing agent for a lysine diisocyanate/PEG/glycerol polyurethane (see Zhang, et al., *Tissue Eng.* 2003 (6): 1143-57) and may also be used to form porous structures in polyurethanes. Other blowing agents include dry ice or other agents that release carbon dioxide or other gases into the composite. Alternatively, or in addition, porogens (see detail discussion below) such as salts may be mixed in with reagents and then dissolved after polymerization to leave behind small voids.

Two-component compositions and/or the prepared composites used in the present invention may include one or more additional components. In some embodiments, inventive compositions and/or composites may includes, water, a catalyst (e.g., gelling catalyst, blowing catalyst, etc.), a stabilizer, a plasticizer, a porogen, a chain extender (for making of polyurethanes), a pore opener (such as calcium stearate, to control pore morphology), a wetting or lubricating agent, etc. (See, U.S. Ser. No. 10/759,904 published under No. 2005-0013793, and U.S. Ser. No. 11/625,119 published under No. 2007-0191963; both of which are incorporated herein by reference).

In some embodiments, inventive compositions and/or composites may include and/or be combined with a solid filler (e.g., carboxymethylcellulose (CMC) and hyaluronic acid (HA)). For example, when composites used in wound healing, solid fillers can help absorb excess moisture in the wounds from blood and serum and allow for proper foaming.

In certain embodiments, additional biocompatible polymers (e.g., PEG) or co-polymers can be used with compositions and composites in the present invention.

Water.

Water may be a blowing agent to generate porous polyurethane-based composites. Porosity of bone/polymer composites increased with increasing water content, and biodegradation rate accelerated with decreasing polyester half-life, thereby yielding a family of materials with tunable properties that are usefull in the present invention. See, Guelcher et al., Tissue Engineering, 13(9), 2007, pp 2321-2333, which is incorporated by reference.

In some embodiments, an amount of water is about 0.5, 1, 1.5, 2, 3, 4 5, 6, 7, 8, 9, 10 parts per hundred parts (pphp) polyol. In some embodiments, water has an approximate rang of any of such amounts.

Catalyst.

In some embodiments, at least one catalyst is added to form reactive liquid mixture (i.e., two-component compositions). A catalyst, for example, can be non-toxic (in a concentration that may remain in the polymer).

A catalyst can, for example, be present in two-component compositions in a concentration in the range of approximately 0.5 to 5 parts per hundred parts polyol (pphp) and, for example, in the range of approximately 0.5 to 2, or 2 to 3 pphp. A catalyst can, for example, be an amine compound. In some embodiments, catalyst may be an organometallic compound or a tertiary amine compound. In some embodiments the catalyst may be stannous octoate (an organobismuth compound), triethylene diamine, bis(dimethylaminoethyl)ether, dimethylethanolamine, dibutyltin dilaurate, and Coscat organometallic catalysts manufactured by Vertullus (a bismuth based catalyst), or any combination thereof.

Stabilizer.

In some embodiments, a stabilizer is nontoxic (in a concentration remaining in the polyurethane foam) and can include a non-ionic surfactant, an anionic surfactant or combinations thereof. For example, a stabilizer can be a polyethersiloxane, a salt of a fatty sulfonic acid or a salt of a fatty acid. In certain embodiments, a stabilizer is a polyethersiloxane, and the concentration of polyethersiloxane in a reactive liquid mixture can, for example, be in the range of approximately 0.25 to 4 parts per hundred polyol. In some embodiments, polyethersiloxane stabilizer are hydrolyzable.

In some embodiments, the stabilizer can be a salt of a fatty sulfonic acid. Concentration of a salt of the fatty sulfonic acid in a reactive liquid mixture can be in the range of approximately 0.5 to 5 parts per hundred polyol. Examples of suitable stabilizers include a sulfated castor oil or sodium ricinoleicsulfonate.

Stabilizers can be added to a reactive liquid mixture of the present invention to, for example, disperse prepolymers, polyols and other additional components, stabilize the rising carbon dioxide bubbles, and/or control pore sizes of inventive composites. Although there has been a great deal of study of stabilizers, the operation of stabilizers during foaming is not completely understood. Without limitation to any mechanism of operation, it is believed that stabilizers preserve the thermodynamically unstable state of a polyurethane foam during the time of rising by surface forces until the foam is hardened. In that regard, foam stabilizers lower the surface tension of the mixture of starting materials and operate as emulsifiers for the system. Stabilizers, catalysts and other polyurethane reaction components are discussed, for example, in Oertel, Günter, ed., *Polyurethane Handbook*, Hanser Gardner Publications, Inc. Cincinnati, Ohio, 99-108 (1994). A specific effect of stabilizers is believed to be the formation of surfactant monolayers at the interface of higher viscosity of bulk phase, thereby increasing the elasticity of surface and stabilizing expanding foam bubbles.

Chain Extender.

To prepare high-molecular-weight polymers, prepolymers are chain extended by adding a short-chain (e.g., <500 g/mol) polyamine or polyol. In certain embodiments, water may act as a chain extender. In some embodiments, addition of chain extenders with a functionality of two (e.g., diols and diamines) yields linear alternating block copolymers.

Plasticizer.

In some embodiments, inventive compositions and/or composites include one or more plasticizers. Plasticizers are typically compounds added to polymers or plastics to soften them or make them more pliable. According to the present invention, plasticizers soften, make workable, or otherwise improve the handling properties of polymers or composites. Plasticizers also allow inventive composites to be moldable at a lower temperature, thereby avoiding heat induced tissue necrosis during implantation. Plasticizer may evaporate or otherwise diffuse out of the composite over time, thereby allowing composites to harden or set. Without being bound to any theory, plasticizer are thought to work by embedding themselves between the chains of polymers. This forces polymer chains apart and thus lowers the glass transition temperature of polymers. In general, the more plasticizer added, the more flexible the resulting polymers or composites will be.

In some embodiments, plasticizers are based on an ester of a polycarboxylic acid with linear or branched aliphatic alcohols of moderate chain length. For example, some plasticizers are adipate-based. Examples of adipate-based plasticizers include bis(2-ethylhexyl)adipate (DOA), dimethyl adipate (DMAD), monomethyl adipate (MMAD), and dioctyl adipate (DOA). Other plasticizers are based on maleates, sebacates, or citrates such as bibutyl maleate (DBM), diisobutylmaleate (DIBM), dibutyl sebacate (DBS), triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC), and trimethylcitrate (TMC). Other plasticizers are phthalate based. Examples of phthalate-based plasticizers are N-methyl phthalate, bis(2-ethylhexyl) phthalate (DEHP), diisononyl phthalate (DINP), bis(n-butyl)phthalate (DBP), butyl benzyl phthalate (BBzP), diisodecyl phthalate (DOP), diethyl phthalate (DEP), diisobutyl phthalate (DIBP), and di-n-hexyl phthalate. Other suitable plasticizers include liquid polyhydroxy compounds such as glycerol, polyethylene glycol (PEG), triethylene glycol, sorbitol, monacetin, diacetin, and mixtures thereof. Other plasticizers include trimellitates (e.g., trimethyl trimellitate (TMTM), tri-(2-ethylhexyl)trimellitate (TEHTM-MG), tri-(n-octyl,n-decyl)trimellitate (ATM), tri-(heptyl,nonyl)trimellitate (LTM), n-octyl trimellitate (OTM)), benzoates, epoxidized vegetable oils, sulfonamides (e.g., N-ethyl toluene sulfonamide (ETSA), N-(2-hydroxypropyl)benzene sulfonamide (HP BSA), N-(n-butyl)butyl sulfonamide (BBSA-NBBS)), organophosphates (e.g., tricresyl phosphate (TCP), tributyl phosphate (TBP)), glycols/polyethers (e.g., triethylene glycol dihexanoate, tetraethylene glycol diheptanoate), and polymeric plasticizers. Other plasticizers are described in *Handbook of Plasticizers* (G. Wypych, Ed., ChemTec Publishing, 2004), which is incorporated herein by reference. In certain embodiments, other polymers are added to the composite as plasticizers. In certain particular embodiments, polymers with the same chemical structure as those used in the composite are used but with lower molecular weights to soften the overall composite. In other embodiments, different polymers with lower melting points and/or lower viscosities than those of the polymer component of the composite are used.

In some embodiments, polymers used as plasticizer are poly(ethylene glycol) (PEG). PEG used as a plasticizer is typically a low molecular weight PEG such as those having an average molecular weight of 1000 to 10000 g/mol, for example, from 4000 to 8000 g/mol. In certain embodiments, PEG 4000, PEG 5000, PEG 6000, PEG 7000, PEG 8000 or combinations thereof are used in inventive composites. For example, plasticizer (PEG) is useful in making more moldable composites that include poly(lactide), poly(D,L-lactide), poly(lactide-co-glycolide), poly(D,L-lactide-co-glycolide), or poly(caprolactone). Plasticizer may comprise 1-40% of inventive composites by weight. In some embodiments, the plasticizer is 10-30% by weight. In some embodiments, the plasticizer is approximately 10%, 15%, 20%, 25%, 30% or 40% by weight. In other embodiments, a plasticizer is not used in the composite. For example, in some polycaprolactone-containing composites, a plasticizer is not used.

In some embodiments, inert plasticizers may be used. In some embodiments, a plasticizer may not be used in the present invention.

Porogen.

Porosity of inventive composites may be accomplished using any means known in the art. Exemplary methods of creating porosity in a composite include, but are not limited to, particular leaching processes, gas foaming processing, supercritical carbon dioxide processing, sintering, phase transformation, freeze-drying, cross-linking, molding, porogen melting, polymerization, melt-blowing, and salt fusion (Murphy et al., *Tissue Engineering* 8(1):43-52, 2002; incorporated herein by reference). For a review, see Karageorgiou et al., *Biomaterials* 26:5474-5491, 2005; incorporated herein by reference. Porosity may be a feature of inventive composites during manufacture or before implantation, or porosity may only be available after implantation. For example, a implanted composite may include latent pores. These latent pores may arise from including porogens in the composite.

Porogens may be any chemical compound that will reserve a space within the composite while the composite is being molded and will diffuse, dissolve, and/or degrade prior to or after implantation or injection leaving a pore in the composite. Porogens may have the property of not being appreciably changed in shape and/or size during the procedure to make the composite moldable. For example, a porogen should retain its shape during the heating of the composite to make it moldable. Therefore, a porogen does not melt upon heating of the composite to make it moldable. In certain embodiments, a porogen has a melting point greater than about 60° C., greater than about 70° C., greater than about 80° C., greater than about 85° C., or greater than about 90° C.

Porogens may be of any shape or size. A porogen may be spheroidal, cuboidal, rectangular, elonganted, tubular, fibrous, disc-shaped, platelet-shaped, polygonal, etc. In certain embodiments, the porogen is granular with a diameter ranging from approximately 100 microns to approximately 800 microns. In certain embodiments, a porogen is elongated, tubular, or fibrous. Such porogens provide increased connectivity of pores of inventive composite and/or also allow for a lesser percentage of the porogen in the composite.

Amount of porogens may vary in inventive composite from 1% to 80% by weight. In certain embodiments, the plasticizer makes up from about 5% to about 80% by weight of the composite. In certain embodiments, a plasticizer makes up from about 10% to about 50% by weight of the composite. Pores in inventive composites are thought to improve the osteoinductivity or osteoconductivity of the composite by providing holes for cells such as osteoblasts, osteoclasts, fibroblasts, cells of the osteoblast lineage, stem cells, etc. Pores provide inventive composites with biological in growth capacity. Pores may also provide for easier degradation of inventive composites as bone is formed and/or remodeled. In some embodiments, a porogen is biocompatible.

A porogen may be a gas, liquid, or solid. Exemplary gases that may act as porogens include carbon dioxide, nitrogen, argon, or air. Exemplary liquids include water, organic solvents, or biological fluids (e.g., blood, lymph, plasma). Gaseous or liquid porogen may diffuse out of the osteoimplant before or after implantation thereby providing pores for biological in-growth. Solid porogens may be crystalline or amorphous. Examples of possible solid porogens include water soluble compounds. Exemplary porogens include carbohydrates (e.g., sorbitol, dextran (poly(dextrose)), starch), salts, sugar alcohols, natural polymers, synthetic polymers, and small molecules.

In some embodiments, carbohydrates are used as porogens in inventive composites. A carbohydrate may be a monosaccharide, disaccharide, or polysaccharide. The carbohydrate may be a natural or synthetic carbohydrate. In some embodiments, the carbohydrate is a biocompatible, biodegradable carbohydrate. In certain embodiments, the carbohydrate is a polysaccharide. Exemplary polysaccharides include cellulose, starch, amylose, dextran, poly(dextrose), glycogen, etc.

In certain embodiments, a polysaccharide is dextran. Very high molecular weight dextran has been found particularly useful as a porogen. For example, the molecular weight of the dextran may range from about 500,000 g/mol to about 10,000,000 g/mol, preferably from about 1,000,000 g/mol to about 3,000,000 g/mol. In certain embodiments, the dextran has a molecular weight of approximately 2,000,000 g/mol. Dextrans with a molecular weight higher than 10,000,000 g/mol may also be used as porogens. Dextran may be used in any form (e.g., particles, granules, fibers, elongated fibers) as a porogen. In certain embodiments, fibers or elongated fibers of dextran are used as a porogen in inventive composites. Fibers of dextran may be formed using any known method including extrusion and precipitation. Fibers may be prepared by precipitation by adding an aqueous solution of dextran (e.g., 5-25% dextran) to a less polar solvent such as a 90-100% alcohol (e.g., ethanol) solution. The dextran precipitates out in fibers that are particularly useful as porogens in the inventive composite. Once the composite with dextran as a porogen is implanted into a subject, the dextran dissolves away very quickly. Within approximately 24 hours, substantially all of dextran is out of composites leaving behind pores in the osteoimplant composite. An advantage of using dextran in a composite is that dextran exhibits a hemostatic property in extravascular space. Therefore, dextran in a composite can decrease bleeding at or near the site of implantation.

Small molecules including pharmaceutical agents may also be used as porogens in the inventive composites. Examples of polymers that may be used as plasticizers include poly(vinyl pyrollidone), pullulan, poly(glycolide), poly(lactide), and poly(lactide-co-glycolide). Typically low molecular weight polymers are used as porogens. In certain embodiments, a porogen is poly(vinyl pyrrolidone) or a derivative thereof. Plasticizers that are removed faster than the surrounding composite can also be considered porogens.

Components to Deliver

Alternatively or additionally, composites of the present invention may have one or more components to deliver when implanted, including biomolecules, small molecules, bioactive agents, etc., to promote bone growth and connective tissue regeneration, and/or to accelerate healing. Examples of materials that can be incorporated include chemotactic factors, angiogenic factors, bone cell inducers and stimulators, including the general class of cytokines such as the TGF-β superfamily of bone growth factors, the family of bone morphogenic proteins, osteoinductors, and/or bone marrow or bone forming precursor cells, isolated using standard techniques. Sources and amounts of such materials that can be included are known to those skilled in the art.

Biologically active materials, comprising biomolecules, small molecules, and bioactive agents may also be included in inventive composites to, for example, stimulate particular metabolic functions, recruit cells, or reduce inflammation. For example, nucleic acid vectors, including plasmids and viral vectors, that will be introduced into the patient's cells and cause the production of growth factors such as bone morphogenetic proteins may be included in a composite. Biologically active agents include, but are not limited to, antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxyapatite, and penetraction enhancer. Additional exemplary substances include chemotactic factors, angiogenic factors, analgesics, antibiotics, anti-inflammatory agents, bone morphogenic proteins, and other growth factors that promote cell-directed degradation or remodeling of the polymer phase of the composite and/or development of new tissue (e.g., bone). RNAi or other technologies may also be used to reduce the production of various factors.

In some embodiments, inventive composites include antibiotics. Antibiotics may be bacteriocidal or bacteriostatic. An anti-microbial agent may be included in composites. For example, anti-viral agents, anti-protazoal agents, anti-parasitic agents, etc. may be include in composites. Other suitable biostatic/biocidal agents include antibiotics, povidone, sugars, and mixtures thereof. Exemplary antibiotics include, but not limit to, Amikacin, Gentamicin, Kanamycin, Neomycin, Netilmicin, Streptomycin, Tobramycin, Paromomycin, Geldanamycin, Herbimycin, Loravabef, etc. (See, *The Merck Manual of Medical Information—Home Edition,* 1999).

Inventive composites may also be seeded with cells. In some embodiments, a patient's own cells are obtained and used in inventive composites. Certain types of cells (e.g., osteoblasts, fibroblasts, stem cells, cells of the osteoblast lineage, etc.) may be selected for use in the composite. Cells may be harvested from marrow, blood, fat, bone, muscle, connective tissue, skin, or other tissues or organs. In some embodiments, a patient's own cells may be harvested, optionally selected, expanded, and used in the inventive composite. In other embodiments, a patient's cells may be harvested, selected without expansion, and used in the inventive composite. Alternatively, exogenous cells may be employed. Exemplary cells for use with the invention include mesenchymal stem cells and connective tissue cells, including osteoblasts, osteoclasts, fibroblasts, preosteoblasts, and partially differentiated cells of the osteoblast lineage. Cells may be genetically engineered. For example, cells may be engineered to produce a bone morphogenic protein.

In some embodiments, inventive composites may include a composite material comprising a component to deliver. For example, a composite materials can be a biomolecule (e.g., a protein) encapsulated in a polymeric microsphere or nanoparticles. In certain embodiments, BMP-2 encapsulated in PLGA microspheres may be embedded in a bone/polyurethane composite used in accordance with the present invention. Sustained release of BMP-2 can be achieved due to the diffusional barriers presented by both the PLGA and Polyurethane of the inventive composite. Thus, release kinetics of growth factors (e.g., BMP-2) can be tuned by varying size of PLGA microspheres and porosity of polyurethane composite.

To enhance biodegradation in vivo, composites of the present invention can also include different enzymes. Examples of suitable enzymes or similar reagents are proteases or hydrolases with ester-hydrolyzing capabilities. Such enzymes include, but are not limited to, proteinase K, bromelaine, pronase E, cellulase, dextranase, elastase, plasmin streptokinase, trypsin, chymotrypsin, papain, chymopapain, collagenase, subtilisin, chlostridopeptidase A, ficin, carboxypeptidase A, pectinase, pectinesterase, an oxireductase, an oxidase, or the like. The inclusion of an appropriate amount of such a degradation enhancing agent can be used to regulate implant duration.

Components to deliver may not be covalently bonded to a component of the composite. In some embodiments, components may be selectively distributed on or near the surface of inventive composites using the layering techniques described above. While surface of inventive composite will be mixed somewhat as the composite is manipulated in implant site, thickness of the surface layer will ensure that at least a portion of the surface layer of the composite remains at surface of the implant. Alternatively or in addition, biologically active components may be covalently linked to the bone particles before combination with the polymer. As discussed above, for example, silane coupling agents having amine, carboxyl, hydroxyl, or mercapto groups may be attached to the bone particles through the silane and then to reactive groups on a biomolecule, small molecule, or bioactive agent.

Preparation of Composite

In general, inventive composites are prepared by combining particles, polymers and optionally any additional components. To form inventive composites, particles as discussed herein may be combined with a reactive liquid (i.e., a two-component composition) thereby forming a naturally injectable or moldable composite or a composite that can be made injectable or moldable. Alternatively, particles may be combined with polyisocyanate prepolymers or polyols first and then combined with other components.

In some embodiments, particles may be combined first with a hardener that includes polyols, water, catalysts and optionally a solvent, a diluent, a stabilizer, a porogen, a plasticizer, etc., and then combined with a polyisocyanate prepolymer. In some embodiments, a hardener (e.g., a polyol, water and a catalyst) may be mixed with a prepolymer, followed by addition of particles. In some embodiments, in order to enhance storage stability of two-component compositions, the two (liquid) component process may be modified to an alternative three (liquid)-component process wherein a catalyst and water may be dissolved in a solution separating from reactive polyols. For example, polyester polyols may be first mixed with a solution of a catalyst and water, followed by addition of bone particles, and finally addition of NCO-terminated prepolymers.

In some embodiments, additional components or components to be delivered may be combined with a reactive liquid prior to injection. In some embodiments, they may be combined with one of polymer precursors (i.e., prepolymers and polyols) prior to mixing the precursors in forming of a reactive liquid/paste.

Porous composites can be prepared by incorporating a small amount (e.g., <5 wt %) of water which reacts with prepolymers to form carbon dioxide, a biocompatible blowing agent. Resulting reactive liquid/paste may be injectable through a 12-ga syringe needle into molds or targeted site to set in situ. In some embodiments, gel time is great than 3 min, 4 min, 5 min, 6 min, 7 min, or 8 min. In some embodiments, cure time is less than 20 min, 18 min, 16 min, 14 min, 12 min, or 10 min.

In some embodiments, catalysts can be used to assist forming porous composites. In general, the more blowing catalyst used, the high porosity of inventive composites may be achieved. In certain embodiments, surprisingly, surface demineralized bone particles may have a dramatic effect on the porosity. Without being bound to any theory, it is believed that the lower porosities achieved with surface demineralized bone particles in the absence of blowing catalysts result from adsorption of water to the hygroscopic demineralized layer on the surface of bones.

Polymers and particles may be combined by any method known to those skilled in the art. For example, a homogenous mixture of polymers and/or polymer precursors (e.g., prepolymers, polyols, etc.) and particles may be pressed together at ambient or elevated temperatures. At elevated temperatures, a process may also be accomplished without pressure. In some embodiments, polymers or precursors are not held at a temperature of greater than approximately 60° C. for a significant time during mixing to prevent thermal damage to any biological component (e.g., growth factors or cells) of a composite. In some embodiments, temperature is not a concern because particles and polymer precursors used in the present invention have a low reaction exotherm.

Alternatively or in addition, particles may be mixed or folded into a polymer softened by heat or a solvent. Alternatively, a moldable polymer may be formed into a sheet that is then covered with a layer of particles. Particles may then be forced into the polymer sheet using pressure. In another embodiment, particles are individually coated with polymers or polymer precursors, for example, using a tumbler, spray coater, or a fluidized bed, before being mixed with a larger quantity of polymer. This facilitates even coating of the particles and improves integration of the particles and polymer component of the composite.

After combination with particles, polymers may be further modified by further cross-linking or polymerization to form a composite in which the polymer is covalently linked to the particles. In some embodiments, composition hardens in a solvent-free condition. In some embodiments, compositions are a polymer/solvent mixture that hardens when a solvent is removed (e.g., when a solvent is allowed to evaporate or diffuse away). Exemplary solvents include but are not limited to alcohols (e.g., methanol, ethanol, propanol, butanol, hexanol, etc.), water, saline, DMF, DMSO, glycerol, and PEG. In certain embodiments, a solvent is a biological fluid such as blood, plasma, serum, marrow, etc. In certain embodiments, an inventive composite is heated above the melting or glass transition temperature of one or more of its components and becomes set after implantation as it cools. In certain embodiments, an inventive composite is set by exposing a composite to a heat source, or irradiating it with microwaves, IR rays, or UV light. Particles may also be mixed with a polymer that is sufficiently pliable to combine with the particles but that may require further treatment, for example, combination with a solvent or heating, to become a injectable or moldable composition. For example, a composition may be combined and injection molded, injected, extruded, laminated, sheet formed, foamed, or processed using other techniques known to those skilled in the art. In some embodiments, reaction injection molding methods, in which polymer precursors (e.g., polyisocyanate prepolymer, a polyol) are separately charged into a mold under precisely defined conditions, may be employed. For example, bone particles may be added to a precursor, or it may be separately charged into a mold and precursor materials added afterwards. Careful control of relative amounts of various components and reaction conditions may be desired to limit the amount of unreacted material in a composite. Post-cure processes known to those skilled in the art may also be employed. A partially polymerized polyurethane precursor may be more completely polymerized or cross-linked after combination with hydroxylated or aminated materials or included materials (e.g., a particulate, any components to deliver, etc.).

In some embodiments, an inventive composite is produced with a injectable composition and then set in situ. For example, cross-link density of a low molecular weight polymer may be increased by exposing it to electromagnetic radiation (e.g., UV light) or an alternative energy source. Alternatively or additionally, a photoactive cross-linking agent, chemical cross-linking agent, additional monomer, or combinations thereof may be mixed into inventive composites. Exposure to UV light after a composition is injected into an implant site will increase one or both of molecular weight and cross-link density, stiffening polymers (i.e., polyurethanes) and thereby a composite. Polymer components of inventive composites used in the present invention may be softened by a solvent, e.g., ethanol. If a biocompatible solvent is used, polyurethanes may be hardened in situ. In some embodiments, as a composite sets, solvent leaving the composite is released into surrounding tissue without causing undesirable side effects such as irritation or an inflammatory response. In some embodiments, compositions utilized in the present invention becomes moldable at an elevated temperature into a pre-determined shape. Composites may become set when composites are implanted and allowed to cool to body temperature (approximately 37° C.).

The invention also provides methods of preparing inventive composites by combining bone particles and polyurethane precursors and resulting in naturally flowable compositions. Alternatively or additionally, the invention provides methods to make a porous composite include adding a solvent or pharmaceutically acceptable excipient to render a flowable or moldable composition. Such a composition may then be injected or placed into the site of implantation. As solvent or excipient diffuses out of the composite, it may become set in place.

Polymer processing techniques may also be used to combine particles with a polyurethane or precursors (e.g., polyisocyanates and polyols). In some embodiments, a composition of polyurethane may be rendered formable (e.g., by heating or with a solvent) and combined with particles by injection molding or extrusion forming. Alternatively, polyurethanes and bone particles may be mixed in a solvent and cast with or without pressure. For example, a solvent may be dichloromethane. In some embodiments, a composition of particle and polymer utilized in the present invention is naturally injectable or moldable in a solvent-free condition.

In some embodiments, particles may be mixed with a polymer precursor according to standard composite processing techniques. For example, regularly shaped particles may simply be suspended in a precursor. A polymer precursor may be mechanically stirred to distribute the particles or bubbled with a gas, preferably one that is oxygen- and moisture-free. Once components of a composition are mixed, it may be desirable to store it in a container that imparts a static pressure to prevent separation of the particles and the polymer precursor, which may have different densities. In some embodiments, distribution and particle/polymer ratio may be optimized to produce at least one continuous path through a composite along particles.

Interaction of polymer components with bone particles may also be enhanced by coating individual particles with a polymer precursor before combining them with bulk precursors. The coating enhances the association of the polymer component of the composite with the particles. For example, individual particles may be spray coated with a monomer or prepolymer. Alternatively, the individual particles may be coated using a tumbler—particles and a solid polymer material are tumbled together to coat the particles. A fluidized bed coater may also be used to coat the particles. In addition, the particles may simply be dipped into liquid or powdered polymer precursor. All of these techniques will be familiar to those skilled in the art.

In some embodiments, it may be desirable to infiltrate a polymer or polymer precursor into vascular and/or interstitial structure of bone particles or into bone-derived tissues. Vascular structure of bone includes such structures such as osteocyte lacunae, Haversian canals, Volksmann's canals, canaliculi and similar structures. Interstitial structure of bone particles includes spaces between trabeculae and similar features. Many of monomers and precursors (e.g., polyisocyanate prepolymers, polyols) suggested for use with the invention are sufficiently flowable to penetrate through the channels and pores of trabecular bone. Some may even penetrate into trabeculae or into mineralized fibrils of cortical bone. Thus, it may be necessary to incubate bone particles in polyurethane precursors for a period of time to accomplish infiltration. In certain embodiments, polyurethane itself is sufficiently flowable that it can penetrate channels and pores of bone. In certain embodiments, polyurethane may also be heated or combined with a solvent to make it more flowable for this purpose. Other ceramic materials and/or other bone-substitute materials employed as a particulate phase may also include porosity that can be infiltrated as described herein.

Inventive composites utilized in the present invention may include practically any ratio of polyurethane and bone particles, for example, between about 5 wt % and about 95 wt % bone particles. In some embodiments, composites may include about 40 wt % to about 45 wt % bone particles, about 45 wt % to about 50 wt % bone particles or about 50 wt % to about 55 wt % bone particles. In some embodiments, composites may include about 55 wt % to about 70 wt % bone particles. In some embodiments, composites may include about 70 wt % to about 90 wt % bone particles. In some embodiments, composites may include at least approximately 40 wt %, 45 wt %, 50 wt %, or 55 wt % of bone particles. In certain embodiments, such weight percentages refer to weight of bone particles and other particulates such as calcium phosphate.

In some embodiments, composites may include at least approximately 30 vol %, 35 vol %, 40 vol %, or 50 vol % of bone particles. In some embodiments, a volume percentage of bone particles in composite in accordance with the present invention may be about 30 vol %, 35 vol %, 40 vol %, 50 vol %, 60 vol %, 70 vol % or between any volume percentages of above. In some embodiments, injectable composites in accordance with the present invention may have a volume percentage (fraction) of at least approximately 36 vol % of bone particles and/or other particulate materials (e.g., calcium phosphate). In some embodiments, volume percentages (fractions) of bone particles and/or other particulate materials in porous composites in the present invention may be less than 64 vol %. In certain embodiments, for a certain volume percentage, corresponding weight percentage of bone particles and/or other particulate materials varies depending on density of particulate components.

Desired proportion may depend on factors such as injection sites, shape and size of the particles, how evenly polymer is distributed among particles, desired flowability of composites, desired handling of composites, desired moldability of composites, and mechanical and degradation properties of composites. The proportions of polymers and particles can influence various characteristics of the composite, for example, its mechanical properties, including fatigue strength, the degradation rate, and the rate of biological incorporation. In addition, the cellular response to the composite will vary with the proportion of polymer and particles. In some embodiments, the desired proportion of particles may be determined not only by the desired biological properties of the injected material but by the desired mechanical properties of the injected material. That is, an increased proportion of particles will increase the viscosity of the composite, making it more difficult to inject or mold. A larger proportion of particles having a wide size distribution may give similar properties to a mixture having a smaller proportion of more evenly sized particles.

Inventive composites of the present invention can exhibit high degrees of porosity over a wide range of effective pore sizes. Thus, composites may have, at once, macroporosity, mesoporosity and microporosity. Macroporosity is characterized by pore diameters greater than about 100 microns. Mesoporosity is characterized by pore diameters between about 100 microns about 10 microns; and microporosity occurs when pores have diameters below about 10 microns. In some embodiments, the composite has a porosity of at least about 30%. For example, in certain embodiments, the composite has a porosity of more than about 50%, more than about 60%, more than about 70%, more than bout 80%, or more than about 90%. In some embodiments, inventive composites have a porosity in a range of 30%-40%, 40%-45%, or 45%-50%. Advantages of a porous composite over non-porous composite include, but are not limited to, more extensive cellular and tissue in-growth into the composite, more continuous supply of nutrients, more thorough infiltration of therapeutics, and enhanced revascularization, allowing bone growth and repair to take place more efficiently. Furthermore, in certain embodiments, the porosity of the composite may be used to load the composite with biologically active agents such as drugs, small molecules, cells, peptides, polynucleotides, growth factors, osteogenic factors, etc, for delivery at the implant site. Porosity may also render certain composites of the present invention compressible.

In some embodiments, pores of inventive composite may be over 100 microns wide for the invasion of cells and bony in-growth (Klaitwatter et al., *J. Biomed. Mater. Res. Symp.* 2:161, 1971; which is incorporated herein by reference). In certain embodiments, the pore size may be in a ranges of approximately 50 microns to approximately 750 microns, for example, of approximately 100 microns to approximately 500 microns.

In some embodiments, compressive strength of dry inventive composites may be in an approximate range of 4-10 MPa, while compressive modulus may be in an approximate range of 150-450 MPa. Compressive strength of the wet composites may be in an approximate range of 4-13 MPa, while compressive modulus may be in an approximate 50-350 MPa.

After implantation, inventive composites are allowed to remain at the site providing the strength desired while at the same time promoting healing of the bone and/or bone growth. Polyurethane of composites may be degraded or be resorbed as new bone is formed at the implantation site. Polymer may be resorbed over approximately 1 month to approximately 1 years. Composites may start to be remodeled in as little as a week as the composite is infiltrated with cells or new bone in-growth. A remodeling process may continue for weeks, months, or years. For example, polyurethanes used in accordance with the present invention may be resorbed within about 4-8 weeks, 2-6 months, or 6-12 months. A degradation rate is defined as the mass loss as a function of time, and it can be measured by immersing the sample in phosphate buffered saline or medium and measuring the sample mass as a function of time.

One skilled in the art will recognize that standard experimental techniques may be used to test these properties for a range of compositions to optimize a composite for a desired application. For example, standard mechanical testing instruments may be used to test the compressive strength and stiffness of composites. Cells may be cultured on composites for an appropriate period of time, and metabolic products and amount of proliferation (e.g., the number of cells in comparison to the number of cells seeded) may be analyzed. Weight change of composites may be measured after incubation in saline or other fluids. Repeated analysis will demonstrate whether degradation of a composite is linear or not, and mechanical testing of incubated materials will show changes in mechanical properties as a composite degrades. Such testing may also be used to compare enzymatic and non-enzymatic degradation of a composite and to determine levels of enzymatic degradation. A composite that is degraded is transformed into living bone upon implantation.

Use and Application of Composite

As discussed above, polymers or polymer precursors, and particles may be supplied separately, e.g., in a kit, and mixed immediately prior to implantation, injection or molding. A kit may contain a preset supply of bone particles having, e.g., certain sizes, shapes, and levels of demineralization. Surface of bone particles may have been optionally modified using one or more of techniques described herein. Alternatively, a kit may provide several different types of particles of varying sizes, shapes, and levels of demineralization and that may have been chemically modified in different ways. A surgeon or other health care professional may also combine components in a kit with autologous tissue derived during surgery or biopsy. For example, a surgeon may want to include autogenous tissue or cells, e.g., bone marrow or bone shavings generated while preparing a implant site, into a composite (see more details in co-owned U.S. Pat. No. 7,291,345 and U.S. Ser. No. 11/625,119 published under No. 2007-0191963; both of which are incorporated herein by reference).

Composites of the present invention may be used in a wide variety of clinical applications. A method of preparing and using polyurethanes for orthopedic applications utilized in the present invention may include the steps of providing a curable bone/polyurethane composition, mixing parts of a composition, and curing a composition in a tissue site wherein a composition is sufficiently flowable to permit injection by minimally invasive techniques. In some embodiments, a flowable composition to inject may be pressed by hand or machine. In some embodiments, a moldable composition may be pre-molded and implanted into a target site. Injectable or moldable compositions utilized in the present invention may be processed (e.g., mixed, pressed, molded, etc.) by hand or machine.

Inventive composites and/or compositions may be used as injectable materials with or without exhibiting high mechanical strength (i.e., load-bearing or non-load bearing, respectively). In some embodiments, inventive composites and/or compositions may be used as moldable materials. For example, compositions (e.g., prepolymer, monomers, reactive liquids/pastes, polymers, bone particles, additional components, etc.) in the present invention can be pre-molded into pre-determined shapes. Upon implantation, the pre-molded composite may further cure in situ and provide mechanical strength (i.e., load-bearing). A few examples of potential applications are discussed in more detail below.

In some embodiments, compositions and/or composites of the present invention may be used as a bone void filler. Bone fractures and defects, which result from trauma, injury, infection, malignancy or developmental malformation can be difficult to heal in certain circumstances. If a defect or gap is larger than a certain critical size, natural bone is unable to bridge or fill the defect or gap. These are several deficiencies that may be associated with the presence of a void in a bone. Bone void may compromise mechanical integrity of bone, making bone potentially susceptible to fracture until void becomes ingrown with native bone. Accordingly, it is of interest to fill such voids with a substance which helps voids to eventually fill with naturally grown bone. Open fractures and defects in practically any bone may be filled with composites according to various embodiments without the need for periosteal flap or other material for retaining a composite in fracture or defect. Even where a composite is not required to bear weight, physiological forces will tend to encourage remodeling of a composite to a shape reminiscent of original tissues.

Many orthopedic, periodontal, neurosurgical, oral and maxillofacial surgical procedures require drilling or cutting into bone in order to harvest autologous implants used in procedures or to create openings for the insertion of implants. In either case voids are created in bones. In addition to all the deficiencies associated with bone void mentioned above, surgically created bone voids may provide an opportunity for incubation and proliferation of any infective agents that are introduced during a surgical procedure. Another common side effect of any surgery is ecchymosis in surrounding tissues which results from bleeding of the traumatized tissues. Finally, surgical trauma to bone and surrounding tissues is known to be a significant source of post-operative pain and inflammation. Surgical bone voids are sometimes filled by the surgeon with autologous bone chips that are generated during trimming of bony ends of a graft to accommodate graft placement, thus accelerating healing. However, the volume of these chips is typically not sufficient to completely fill the void. Composites and/or compositions of the present invention, for example composites comprising anti-infective and/or anti-inflammatory agents, may be used to fill surgically created bone voids.

Inventive composites may be administered to a subject in need thereof using any technique known in the art. A subject is typically a patient with a disorder or disease related to bone. In certain embodiments, a subject has a bony defect such as a fracture. In some embodiment, a subject is typically a mammal although any animal with bones may benefit from treatment with the inventive composite. In certain embodiments, a subject is a vertebrate (e.g., mammals, reptiles, fish, birds, etc.). In certain embodiments, a subject is a human. In other embodiments, the subject is a domesticated animal such as a dog, cat, horse, etc. Any bone disease or disorder may be treated using inventive composites/compositions including genetic diseases, congenital abnormalities, fractures, iatrogenic defects, bone cancer, bone metastases, inflammatory diseases (e.g., rheumatoid arthritis), autoimmune diseases, metabolic diseases, and degenerative bone disease (e.g., osteoarthritis). In certain embodiments, inventive osteoimplant composites are formulated for repair of a simple fracture, compound fracture, or non-union; as an external fixation device or internal fixation device; for joint reconstruction, arthrodesis, arthroplasty, or cup arthroplasty of hips; for femoral or humeral head replacement; for femoral head surface replacement or total joint replacement; for repair of vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones, and for repair of bone surrounding cysts and tumors.

Composites and/or compositions of the present invention can be used as bone void fillers either alone or in combination with one or more other conventional devices, for example, to fill the space between a device and bone. Examples of such devices include, but are not limited to, bone fixation plates (e.g., cranofacial, maxillofacial, orthopedic, skeletal, and the like); screws, tacks, clips, staples, nails, pins or rods, anchors (e.g., for suture, bone, and the like), scaffolds, scents, meshes (e.g., rigid, expandable, woven, knitted, weaved, etc), sponges, implants for cell encapsulation or tissue engineering, drug delivery (e.g., carriers, bone ingrowth induction catalysts such as bone morphogenic proteins, growth factors (e.g., PDGF, VEGF and BMP-2), peptides, antivirals, antibiotics, etc), monofilament or multifilament structures, sheets, coatings, membranes (e.g., porous, microporous, resorbable, etc), foams (e.g., open cell or close cell), screw augmentation, cranial, reconstruction, and/or combinations thereof.

These and other aspects of the present invention will be further appreciated upon consideration of the following Examples, which are intended to illustrate certain particular embodiments of the invention but are not intended to limit its scope, as defined by the claims.

EXAMPLES

Example 1

Polyester Macrotriol Synthesis and Characterization $\epsilon$-Caprolactone, the blowing catalyst bis(2-dimethylaminoethyl)ether (DMAEE), the gelling catalyst triethylene diamine (TEDA), dipropylene glycol (DPG), and poly(ethylene glycol) (PEG, MW 200-Da) were all obtained from Sigma-Aldrich (St. Louis, Mo.). Glycolide and D,L-lactide were purchased from Polysciences, Inc. (Warrington, Pa.), and a tertiary amine gelling catalyst (TEGOAMIN33) from Goldschimidt (Hopewell, Va.). Lysine Triisocyanate (LTI) was obtained from Kyowa Hakko USA. Bovine (B-MBP) and human (H-MBP) mineralized bone particles (MBP) with diameters in the range of 106-500 μm were obtained from Osteotech, Inc. (Eatontown, N.J.). With the exception of $\epsilon$-caprolactone, PEG, DMAEE, and glycerol, all materials were used as received. Prior to use, PEG and glycerol were dried at 10 mm Hg for at least 4 hours at 80° C., and $\epsilon$-caprolactone was dried over anhydrous magnesium sulfate. DMAEE was blended with DPG at a 70:30 mass ratio.

Polyester triols of 900-Da molecular weight, T6C3G1L900, were prepared with a trifunctional glycerol starter and 60 wt % $\epsilon$-caprolactone, 30% glycolide, 10% D,L-lactide, and stannous octoate catalyst (0.1%), as previously described. These components were mixed with mechanical stirring in a three-neck flask for 36 hours under argon at 140° C. The product was then dried under vacuum for at least 24 hours at 80° C., followed by preparing a concentrated solution in dichloromethane and washing 3× with hexane (Storey at eL, *Journal of Polymer Science, Part A: Polymer Chemistry* 1994; 32(12):2345-2363).

The OH number was measured by titration according to ASTM D 4274-99 Method C and the molecular weight was measured by GPC (Waters Breeze) using two MesoPore 300× 7.5 mm columns (Polymer Laboratories, Amherst, Mass.) in series and a dichloromethane (DCM) mobile phase. The polyol hardener was produced by mixing the appropriate amounts of T6C3G1L900, deionized (DI) water, DMAEE, and TEGOAMIN33 in a Hauschild SpeedMixer™ DAC 150 FVZ-K vortex mixer (FlackTek, Inc., Landrum, S.C.). In an alternative method, a high NCO quasi-prepolymer was synthesized by adding the polyester to hexamethylene diisocyanate (HDI). The % NCO of the prepolymer was measured by titration using ASTM D 2572-97, and the hydroxyl number calculated from the mass balance and measured % NCO.

The molecular weight and OH number of the polyester macrotriol are listed in Table 1. The number-average molecular weight was measured to be 1405 g/mol, compared to the theoretical value of 900 g/mol. However, GPC is a relative measure of molecular weight, and is therefore not as useful for formulating two-component polyurethanes, which requires the absolute molecular weight. The OH number is a more reliable value for formulating the PUR composition (Storey et al., *Journal of Polymer Science, Part A: Polymer Chemistry* 1994; 32(12):2345-2363). While the theoretical OH number was 187 mg KOH/g, the measured value was 153 mg KOH/g, and the calculated value from the prepolymer % NCO titration was 212 mg KOH/g. Considering that the theoretical value of the OH number was between the two measured values, the theoretical value was used to formulate the polyurethanes, as reported previously (Hafeman et al., *Pharm Res* 2008; 25(10):2387-99; Guelcher et al., *Tissue Engineering* 2007; 13(9):2321-2333).

TABLE 1

Characterization of polyester macrotriol.

| | |
|---|---|
| Theoretical OH number (mg KOH/g) | 187 |
| Measured OH number (mg KOH/g) | 153 |
| OH number calculated from high NCO prepolymer (mg KOH/g) | 212 |
| Theoretical molecular weight (g mol$^{-1}$) | 900 |
| Measured molecular weight (g mol$^{-1}$) | $M_n = 1405$ |
| | $M_w = 2048$ |
| | $M_p = 2036$ |
| | PD = 1.46 |

Example 2

Prepolymer Synthesis and Characterization

The LTI-PEG prepolymer was synthesized by adding poly(ethylene glycol) (200 g/mol, PEG200) dropwise over the course of 1 hour to LTI in a three-neck flask while stirring under argon. The mixture was then stirred for 24 hours at 45° C., and the subsequently dried under vacuum for at least 24 hours at 80° C. The NCO:OH equivalent ratio of the prepolymer was 3.0:1.0. The % NCO was measured by titration according to ASTM D 2572-97, the molecular weight distribution was measured by GPC as described previously, and the viscosity was determined using a Brookfield viscometer. The prepolymer was stored under argon at 4° C.

The % NCO of the prepolymer was measured to be 22.8%, which is in good agreement with the theoretical value of 23%. The viscosity was measured to be 21,000 cP using a Brookfield viscometer. As shown in Table 2, the molecular weight of the prepolymer is broadly distributed, ranging from monomeric LTI to the LTI-PEG-LTI-PEG-LTI-PEG-LTI-PEG-LTI adduct comprising 4 molecules of LTI and 3 molecules of PEG. This observation is consistent with previously reported data for polyurethane prepolymers, which are typically characterized by a broad molecular weight distribution (Oertel G., *Polyurethane Handbook*. Berlin: Hanser Gardner Publications; 1994).

Example 3

Preparation and Characterization of Surface-Demineralized and Defatted Allograft Bone Particles Mineralized bovine bone particles (B-MBP) were sonicated in 0.1M HCl for 90 seconds. An equal volume of DI water was subsequently added. The particles were then filtered, rinsed with DI water, and vacuum-dried. This entire process was repeated for a total of two times, and the particles were subsequently rinsed with 70% ethanol and dried. The resulting surface-demineralized bone particles (SDMBP) were then lyophilized at −50° C. for a minimum of 14 hours at 0.10 mbar. To prepare defatted mineralized bovine bone particles (DBMBP), mineralized bone particles were stirred with a 50/50% volume solution of acetone/chloroform in a volumetric ratio of 1:10 for at least 48 h.

Mineralized human bone particles (H-MBP) were used as received from Osteotech. H-MBP was prepared by comminuting debrided and cleaned cortical bone in a mill. Ground particles were sieved between 106-500 μm diameter and defatted in 70% denatured alcohol for at least an hour. Particles were washed with sterile deionized water, lyophilized for a minimum of 6 hrs at −35° C. followed by a minimum of 12 hrs at 35° C. below 500 mtorr. Lyophilized bone particles were treated with supercritical carbon-dioxide at 105° C. for at least 25 minutes. The bone was packaged under dry argon and gamma irradiated at 25-35 KGy.

B-MBP, SDMBP, DFMBP, and H-MBP were imaged by scanning electron microscopy (Hitachi S-4200 SEM, Finchampstead, UK). The skeletal density, which accounts for both the volume of the solid as well as the blind (e.g., inaccessible) pores, was measured by gas pycnometry using nitrogen as the penetrating gas (Micromeritics, Norcross, Ga.). The skeletal density ($\rho_{MBP}$) was used to calculate the porosity of the composites because it was assumed that the PUR binder would wet the external pores but not the internal (blind) pores. The particle size distribution was measured using a Saturn DigiSizer 5200 V1.12 (Micromeritics, Norcross, Ga.).

The surfaces of B-MBP, SDMBP, DFMBP, and H-MBP were characterized by XPS using a PHI 5000 VersaProbe XPS with a 25 W monochromatic Al K-α X-ray source and a 100-μm spot size. Survey and high resolution spectra were collected using 187.85 and 23.5 eV pass energies respectively. All the measurements were done using a 45° take-off angle and charge neutralization under ultrahigh vacuum. Analysis of the data was performed using the software CasaXPS Version 2.3.14 (© 1999-2008 Neal Fairley).

TABLE 2

Molecular weight distribution of LTI-PEG prepolymer. The "theoretical" value is calculated from the actual molecular weights of LTI and PEG200, and the "calculated" value is calculated from the measured $M_n$ of LTI and PEG and the structure of the component.

| Component | Theoretical $M_n$, g mol$^{-1}$ | Measured $M_n$, g mol$^{-1}$ | Calculated $M_n$, g mol$^{-1}$ | Area % |
|---|---|---|---|---|
| LTI | 269 | 309 | 309 | 16.8 |
| PEG | 200 | 424 | 424 | <0.5 |
| LTI-PEG | 469 | 708 | 733 | <0.5 |
| LTI-PEG-LTI | 738 | 1071 | 1042 | 22.5 |
| LTI-PEG-LTI-PEG-LTI | 1207 | 1788 | 1775 | 17.0 |
| LTI-PEG-LTI-PEG-LTI-PEG-LTI | 1676 | 2470 | 2508 | 11.9 |
| LTI-PEG-LTI-PEG-LTI-PEG-LTI-PEG-LTI | 2145 | 3122 | 3241 | 31.7 |

SEM images of B-MBP, SDMBP, DFMBP, and H-MBP are shown in FIG. 1. The mean particle sizes (measured by SEM) and skeletal densities (measured by helium pycnometry) are listed in Table 3. Considering that defatting and surface-demineralization only affected the external surfaces of the particles, these processes had negligible effects on the skeletal density or mean size of the particles. The compositions of the surfaces of the bone particles, as measured by XPS, are also presented in Table 3. B-MBP was extensively covered with a layer of fat, as evidenced by the high carbon content and low oxygen, calcium, and phosphorous concentration. Defatting the bone successfully removed the layer of fat on the surface, as shown by the reduction in carbon and increase in oxygen, calcium, and phosphorous concentrations. Similarly, surface-demineralization effectively removed the mineral content from the surface of the allograft particles. The surface of B-SDMBP is depleted in calcium and phosphorous but enriched in carbon and nitrogen, indicating that the surface of the allograft has been partially demineralized.

Characterization of bovine and human allograft bone particles.

$$\varepsilon = 1 - \frac{\bar{\rho}}{\rho_c} \quad (1)$$

where $\bar{\rho}$ is the average measured composite foam density (cored) and $\rho_c$ is the density of the composite assuming there are no pores:

$$\rho_c = \frac{1}{\frac{x_B}{\rho_B} + \frac{1-x_B}{\rho_P}} \quad (2)$$

where $\varepsilon$ is the porosity, $\rho_F$ is scaffold density, $\rho_{MBP}=2100$ kg-m$^{-3}$ is the density of MBP (measured by pycnometry), $\rho_{PUR}=1200$ kg-m$^{-3}$ is the density of PUR (measured gravimetrically), and $x_{MBP}$ is the weight fraction of MBP. Data are presented as mean±standard deviation of triplicate samples. Scanning electron microscope (SEM) micrographs, used to determine pore size, were obtained using a Hitachi S-4200 (Finchampstead, UK).

| Material | Mean size µm | Density g cm$^{-3}$ | XPS % C | XPS % O | XPS % Ca | XPS % P | XPS % N |
|---|---|---|---|---|---|---|---|
| B-MBP | 175 ± 91 | 2.133 | 86.1 ± 2.16 | 11.8 ± 1.49 | 1.04 ± 0.50 | 0.48 ± 0.20 | 0.97 ± 0.25 |
| DFMBP | N/A | 2.199 | 51.6 ± 0.35 | 31.1 ± 0.57 | 6.75 ± 0.49 | 4.5 ± 0.42 | 6.05 ± 0.07 |
| SDMBP | N/A | 2.130 | 57.4 ± 2.62 | 25.1 ± 1.98 | 3.15 ± 0.78 | 1.85 ± 0.64 | 12.6 ± 0.78 |
| H-MBP | 98 ± 48 | 2.18 | 45.9 ± 4.2 | 33.4 ± 3.3 | 7.03 ± 1.15 | 4.57 ± 0.35 | 9.07 ± 0.50 |

Example 4

Synthesis and Characterization of the Injectable MBP/PUR Composite Void Filler

To prepare the void filler, the hardener, LTI-PEG prepolymer, and SDMBP were charged to a mixing cup and hand-mixed for 1 minute. Composites incorporating bovine bone were prepared with 50 wt % (36 vol %) allograft particles, the maximum that could be successfully injected using the 5-ml syringe (for H-MBP it was 45 wt % (30 vol %)).

The relative amounts of the prepolymer and hardener components were calculated assuming an index of 115 (the index is defined as 100× (no. of NCO equivalents/no. of OH equivalents)) (Guelcher et al., Tissue Eng 2006; 12(5):1247-1259). The OH titration, NCO titration, and GPC measurement yielded different values of the OH number that bracketed the theoretical OH number; therefore, the theoretical OH number was used to formulate the composites. This approach has been reported to yield PUR scaffolds with minimal sol fraction when indexed at 115 (Guelcher et al., Tissue Eng 2006; 12(5):1247-1259).

Figure 2:
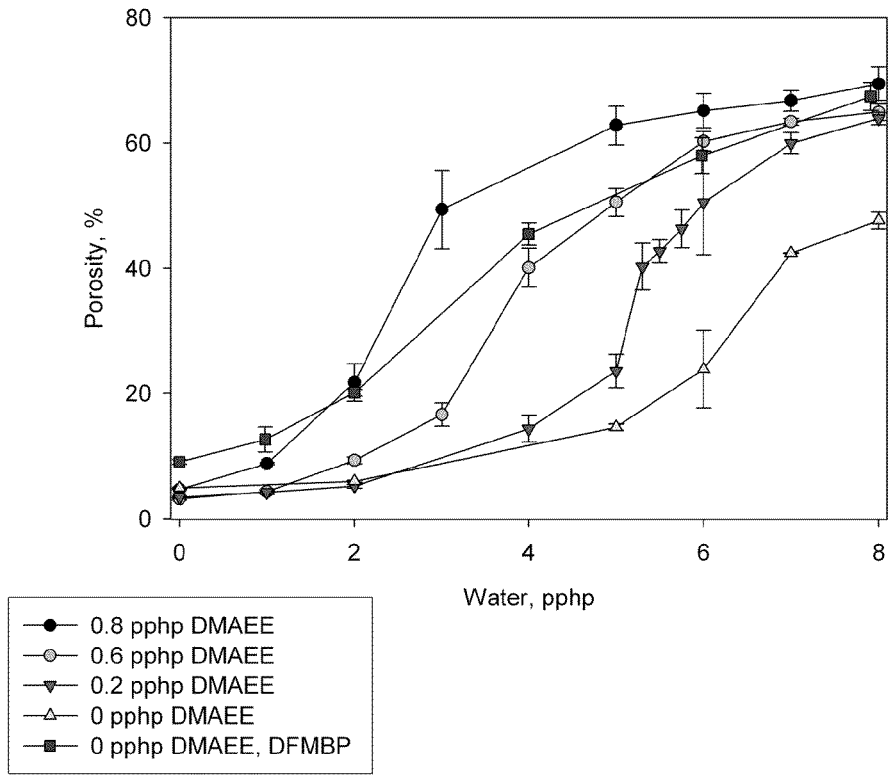
FIG. 2 illustrates SDMBP/PUR scaffold porosity as a function of water concentration at varying concentrations of DMAEE. The TEGOAMIN concentration was 1.8 pphp (0.6 pphp TEDA) for all samples. Data are presented as mean±standard deviation of triplicate samples.

The resulting reactive paste was subsequently transferred into a 5-ml syringe and injected into a mold. The composites were cured overnight at ambient temperature prior to the density measurements. The density of the scaffolds was determined from mass and volume measurements of triplicate cylindrical samples with 12 mm diameters and lengths varying from 15-25 mm. The porosity, defined as the volume fraction pores, was calculated from the composite foam density (Guelcher et al., Tissue Engineering 2006; 12(5):1247-1259), which was measured gravimetrically:

The density of the injectable composites was adjusted by varying the concentrations of the catalysts and water, as well as the processing technique. In preliminary experiments with SDMBP, allograft composite foams were prepared using published techniques, wherein a hardener was first prepared by combining the polyester triol, catalyst, and water to form a hardener component (Guelcher et al., Tissue Eng 2006; 12(5): 1247-1259; Guelcher et al., Tissue Engineering 2007; 13(9): 2321-2333). While previous studies required the use of a fatty acid-derived stabilizer and pore opener to generate small (e.g., <1 mm) pores, scaffolds synthesized from LTI-PEG prepolymer did not require these components to achieve the targeted porosity and pore size distribution. The SDMBP component was added to the hardener and mixed by hand for 30 s, followed by addition of the prepolymer and mixing for 60 s. The material was then charged to a 3 ml syringe and injected into a mold. As shown in FIG. 2a, in the presence of the tertiary amine catalyst triethylene diamine (TEDA, added at a concentration of 0.8 parts per hundred parts polyol (pphp) as a 33% solution in triethylene glycol), the porosity of SDMBP/PUR composites varied over the range of 2-48%. Even at higher water concentrations it was not possible to increase the porosity beyond 50%. TEDA is a potent gelling catalyst that preferentially catalyzes the isocyanate-polyol reaction, but it also has some activity toward the isocyanate-water blowing reaction (Oertel G., Polyurethane Handbook. Berlin: Hanser Gardner Publications; 1994). In the presence of DMAEE, the maximum achievable porosity was increased to 70%, which is consistent with the fact that DMAEE is a tertiary amine catalyst that preferentially catalyzes the isocyanate-water blowing reaction relative to the isocyanate-polyol gelling reaction (Oertel G., Polyurethane Handbook. Berlin: Hanser Gardner Publications; 1994). To investigate the effects of surface chemistry of the bovine bone particles on the density of the materials, composite foams were also prepared using bovine DFMBP in the hardener process with no DMAEE. As shown in FIG. 2, the composition of the bone surface had a dramatic effect on the porosity. The lower porosities achieved with SDMBP in the absence of DMAEE are conjectured to result from adsorption of water in the hardener to the hygroscopic demineralized layer on the surface of the bone.

An important limitation of the two-component hardener process is the storage stability of the hardener component. When the hardener component comprising polyol, water, and catalyst was stored for >3 days at 37° C. and subsequently used to prepare composite foams, the resulting materials exhibited dramatic (e.g., >10–2%) changes in porosity. In order to prepare an injectable polyurethane with acceptable storage stability, the two (liquid) component process was modified to an alternative three (liquid)-component process wherein the TEDA catalyst (0.8 pphp) and water were dissolved in a dipropylene glycol (DPG) solution. Another advantage of the three-component process is that the volume of DPG can be increased to yield a sufficiently large solution volume that can be reliably filled in a syringe (e.g., ~200 μl for a clinically relevant batch size of 5 g). Allograft/PUR composite foams were synthesized by first mixing the polyol and DPG+catalyst+water solution for 60 s, followed by addition of allograft particles, and finally addition of the LTI-PEG prepolymer. The resulting reactive paste was mixed for 30 s, charged to a 3-ml syringe, and injected into a 3-ml polypropylene mold. There were no significant differences in the porosity of the composite foams between the two- and three-component processes.

Figure 6:
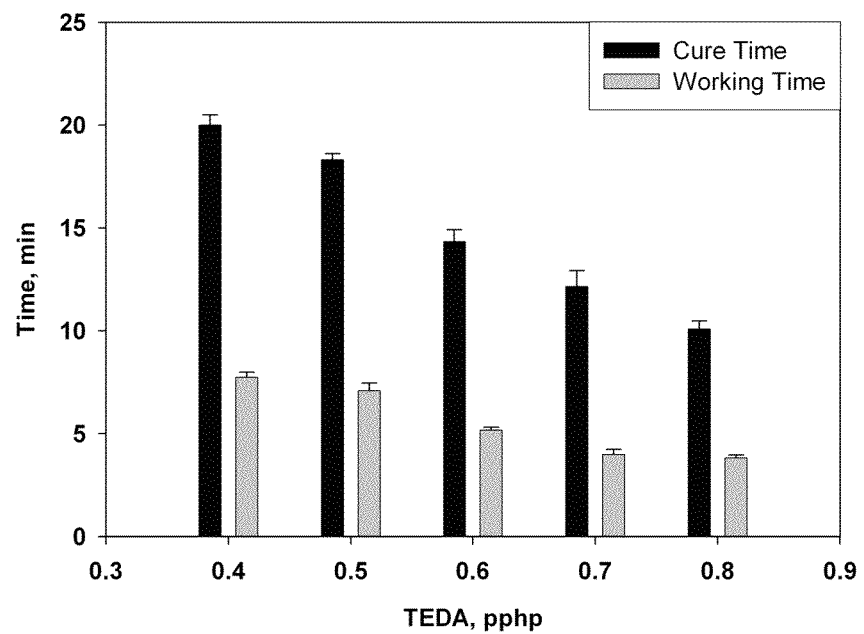
FIG. 6 illustrates the cure and working times of 50 wt % SDMBP/PUR scaffolds with varying TEDA concentrations. DMAEE and water concentrations were 0.6 and 4.0 pphp, respectively.

The working and cure times were adjusted by varying the concentration of TEDA catalyst using the two-component process. At elapsed times shorter than the working time, the mixed components of the scaffold can be injected from the syringe and manipulated without disrupting the pore structure. The tack-free time is the amount of time required for the scaffold to sufficiently cure such that the surface can be touched with a probe that is subsequently removed without adhering to the surface (analogous to the setting time of a calcium phosphate bone cement). As shown in FIG. 6, the tack-free time of the SDMBP/PUR scaffolds (porosity 40%) varied between 10-20 minutes by reducing the TEDA concentration from 0.8 to 0.4 parts per 100 parts polyol (pphp). The working time varied from 4-8 minutes over the same TEDA concentration range. Working and tack-free times were not strongly influenced by water concentration, allograft surface chemistry, or the type of allograft.

Figure 7:
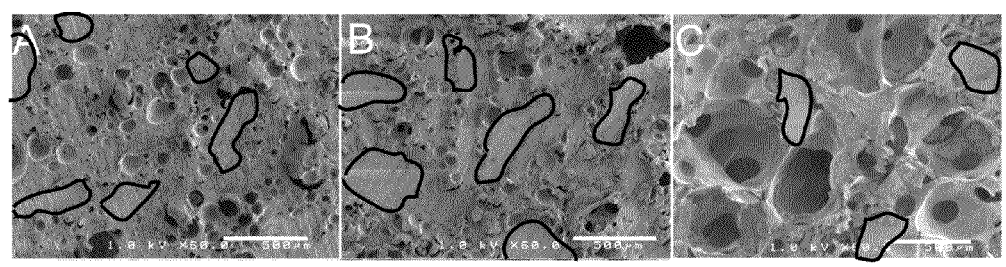
FIG. 7 illustrates SEM micrographs of 50 wt % SDMBP/PUR foam scaffolds at (A) 35%, (B) 47%, and (C) 65% porosity. Example allograft bone particles are traced in black. Scale bar represents 500 μm.

SEM images of the allograft/polymer composites are shown in FIG. 7 for composites with porosities of 35, 47, and 65%. Allograft bone particles (outlined in black) are dispersed throughout the scaffold, and are generally separated from one another by a polymer film. At 35% and 47% porosities, the pores are smaller (~25-250 μm) and are not interconnected. At 65% porosity, the pores are larger (100-500 μm) and appear to be inter-connected, which is consistent with previous studies investigating non-filled scaffolds (Hafeman et al., *Pharmaceutical Research* 2008; 25(10):2387-99.)

Example 5

Mechanical Testing

Cylindrical samples with 12 mm diameters and lengths ranging from 10-30 mm were prepared. Samples that are designated "wet" were submerged in phosphate-buffered saline (PBS) for 24 hours prior to testing. Samples were tested in compression mode using the MTS Bionix system (Eden Prairie, Minn. USA) with 1 kN load cell. The displacement rate was adjusted on a lot-by-lot basis maintain a relatively constant strain rate for all test samples. The displacement rate varied between 2 mm/min and 6 mm/min; this corresponds to a strain rate of approximately 20-25%/min for each test sample. Data are presented as mean±standard deviation of triplicate samples.

One objective of the present study was to synthesize MBP/PUR composite scaffolds at the highest bone fraction that could be injected through a 12-ga syringe needle. While for formulation purposes it is easier to express the bone content in terms of the weight fraction (or wt %), the volume fraction $\phi_{MBP}$ controls the viscosity of the suspension and is calculated from the weight fraction $x_{MBP}$ as follows:

$$\phi_{MBP} = \frac{\frac{x_{MBP}}{\rho_{MBP}}}{\frac{x_{MBP}}{\rho_{MBP}} + \frac{x_{PUR}}{\rho_{PUR}}} \quad (3)$$

The highest weight fraction of bone particles that could be ejected from a standard laboratory 3-ml syringe was found to be 50 wt % (36.0 vol %) for B-MBP and 45 wt % (30 vol %) for H-MBP. Therefore, all subsequent experiments were performed at these conditions.

Figure 3:
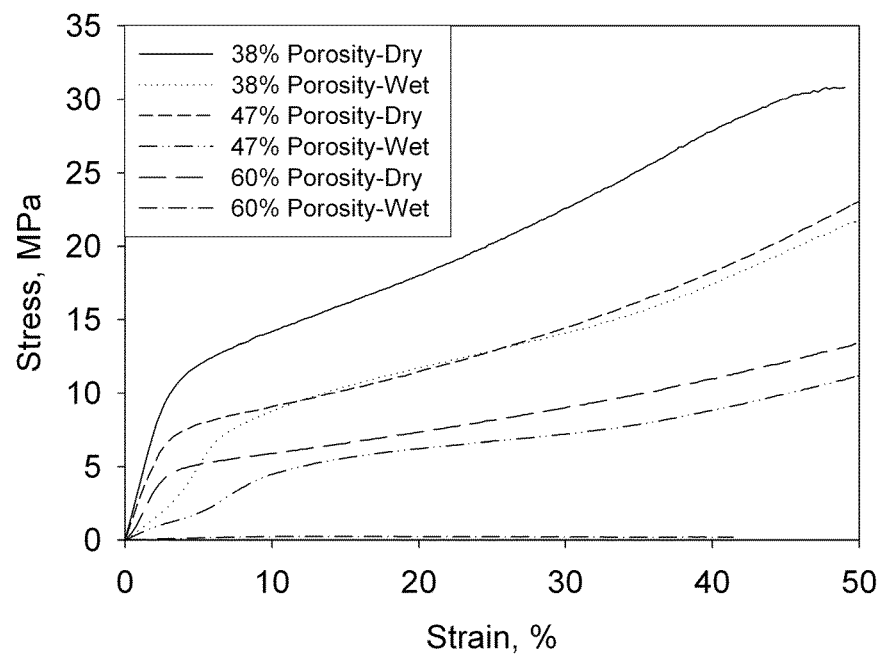
FIG. 3 illustrates compressive stress-strain curves for the 38%, 47%, and 60% porosity scaffolds fabricated from SDMBP.
Figure 4:
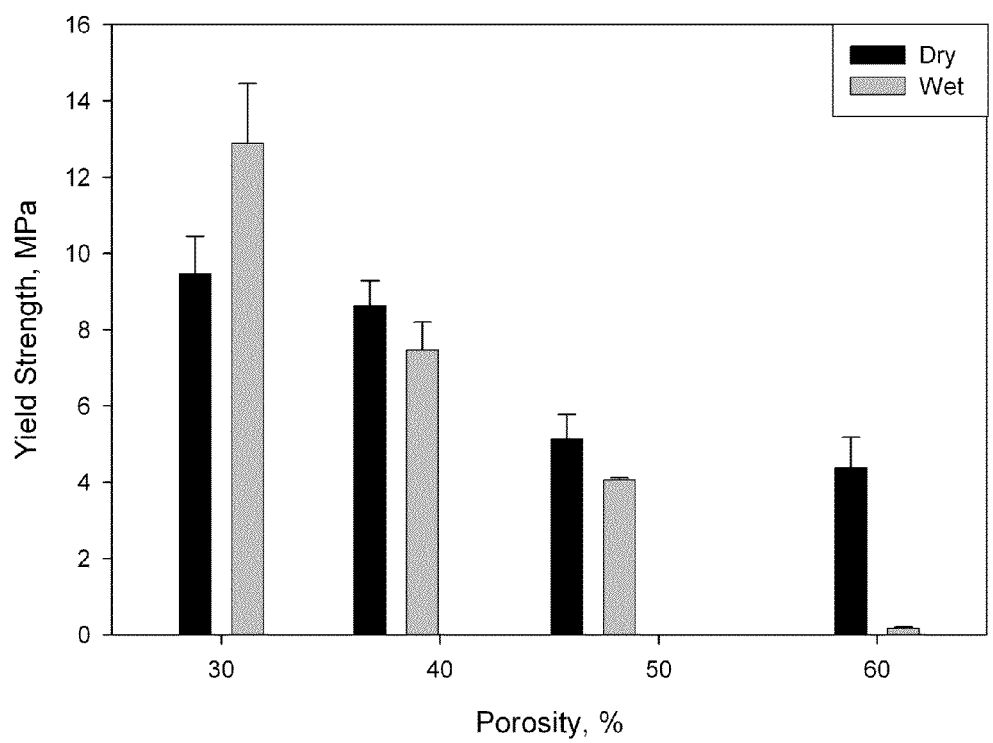
FIG. 4 illustrates compressive strengths of dry and wet 50 wt % (36 vol %) SDMBP/PUR scaffolds at porosities ranging from 30-60%.
Figure 5:
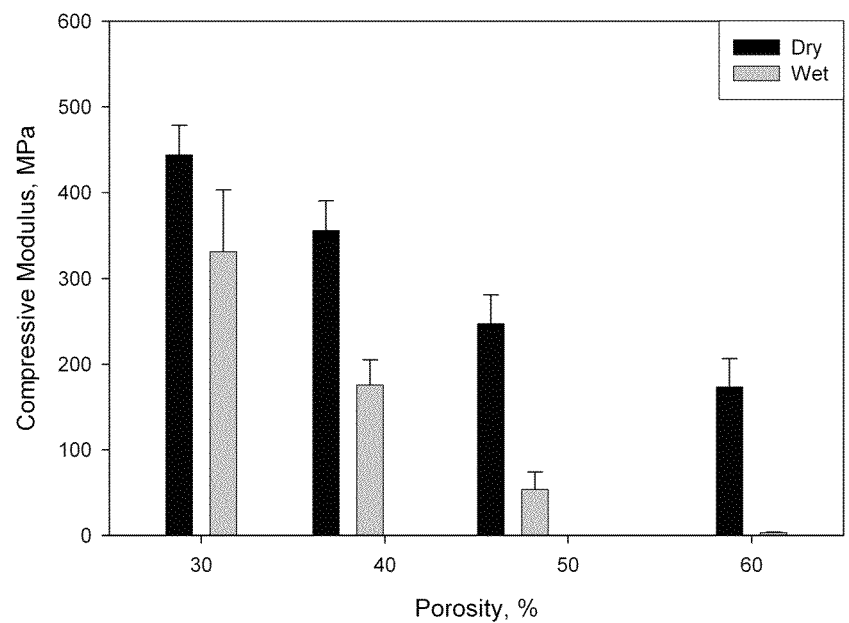
FIG. 5 illustrates compressive moduli of dry and wet 50 wt % (36 vol %) SDMBP/PUR foam scaffolds at varying porosities.

As anticipated, the mechanical properties of the scaffolds are highly dependent on the porosity. FIG. 3 shows the compressive stress-strain curves of the SDBP/PUR scaffolds with porosities ranging from 38-60%. FIG. 4 shows that the compressive strength of the SDBP/PUR dry scaffolds varied from 4.38-9.47 MPa as the porosity was reduced from 50 to 30%. The compressive modulus of the scaffolds ranged from 173.4-444.1 MPa in the same porosity range, as shown in FIG. 5. For the wet samples, the compressive strength of the scaffolds varied from 4.06-12.88 MPa, while the compressive modulus varied from 53.2-331.5 MPa as the porosity decreased from 47 to 30%. However, the wet 60% porosity scaffolds exhibited substantially lower mechanical properties, with compressive strength 0.167 MPa and modulus 3.11 MPa. These compressive properties are in the range previously reported for unfilled PUR scaffolds (Hafeman et al., *Pharm Res* 2008; 25(10):2387-99). For composites with the same porosity, there were no significant differences in modulus or strength between materials prepared from SDMBP or DFMBP (data not shown). Considering that the reinforcement of mechanical properties resulting from the allograft component was retained at porosities ≤50%, the targeted porosity was selected as 40% for future experiments.

Example 6

In Vitro Degradation

Samples (6 mm diameter×1 mm long) were individually placed in small vials, immersed in PBS, and stored at 37° C. under mechanical agitation. At each time point samples were immersed in DI water for at least 1 hour for a total of 2 water changes at room temperature. The samples were then lyophilized at −50° C. and 0.1 mbar for 16 hours, and weighed to determine mass lost. Data are presented as mean±standard deviation of quadruplicate samples.

Figure 8:
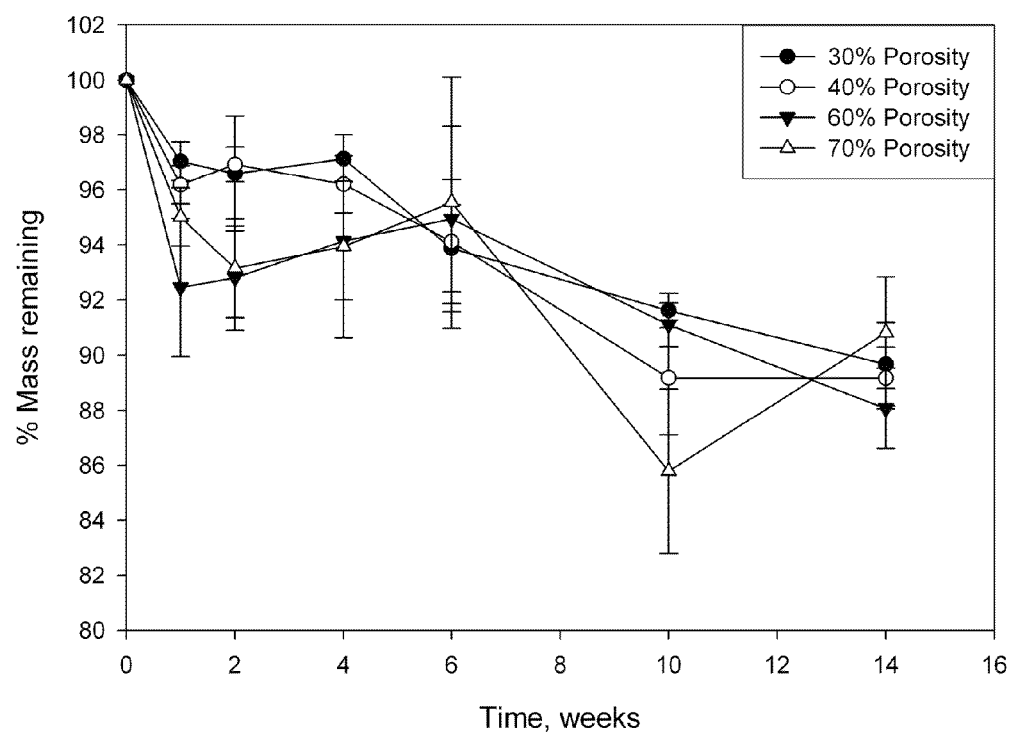
FIG. 8 illustrates in vitro degradation of SDMBP/PUR scaffolds as a function of porosity. Samples were incubated in PBS at 37° C. and mixed end over end, and removed and weighed at each time point.

In vitro degradation data are presented in FIG. 8. At 18 weeks degradation time, the remaining mass of the scaffolds varied from 88-92 wt %, and there were no significant differences in degradation between the four different porosities (30, 40, 60, and 70%).

Example 7

In Vivo Study

The polyol hardener, LTI-PEG prepolymer, and human MBP (H-MBP) were sterilized by gamma irradiation at a dosage of 25-35 kGy. The components were hand-mixed by charging the polyol, allograft bone particles, and prepolymer to a 20-ml cup and mixing for 1 minute. The catalyst solution comprising 5% TEDA and 1.2 pphp water in DPG was subsequently added and the reactive paste mixed for another 30 s. The mixture was transferred to a syringe and injected into 4-mm unicortical femoral plug defects in athymic rats. Two approaches were pursued to investigate the effects of wound closure time on material properties. In one treatment group, the material was injected into the defect and the wound immediately closed. In the second treatment group, the material was injected into the defect and allowed to expand for 15 minutes before the wound was closed. After 3 weeks, the femurs were extracted, fixed in neutral buffered formalin, and imaged by µCT. The bones were then decalcified with 10% formic acid solution followed by dehydration in increasing concentration of alcohol followed by a clearing agent. Finally, samples were soaked in in glycidyl methacrylate (GMA) and embedded in GMA. Post curing, 4-6 µm thin sections were cut, mounted on slides, and stained with toluidene blue/basic fuchsin mixture. Slides were washed in water followed by dehydration in increasing concentration of alcohol followed by a clearing agent. Dehydrated slides were cover-slipped and prepared for micrographs.

Figure 9:
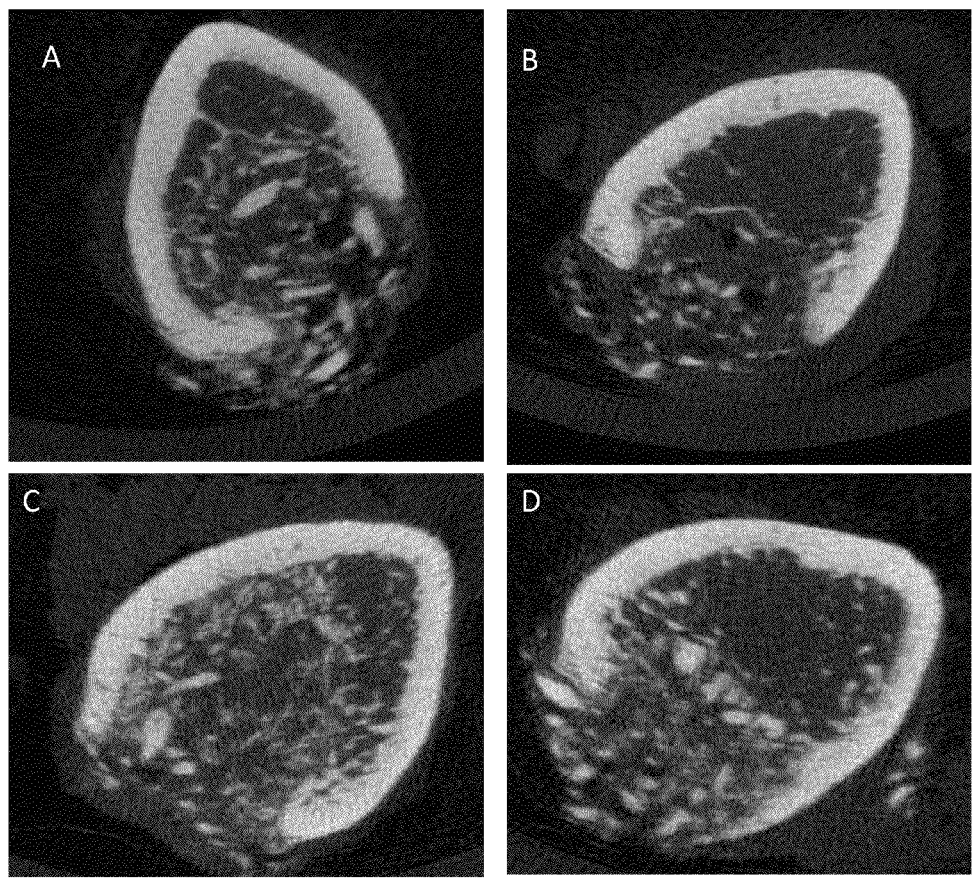
FIG. 9 illustrates μCT images of H-SDMBP/PUR bone void filler injected into plug defects in the distal femurs of athymic rats. (A)-(B): Wound closed immediately after injection. (C)-(D): Wound closed 15 minutes after injection.

A pilot study was performed in an athymic rat model to demonstrate injectability of the material and investigate its potential to support new bone formation. The 40% porosity formulation was selected due to its suitable mechanical properties for weight-bearing applications. Considering that the manufacture of surface-demineralized allograft bone particles is challenging, as well as the observation that the differences in mechanical properties between SDBMP and DFMBP composites were minimal, H-MBP composites were selected for the animal study. The allograft concentration was 45 wt % (30 vol %), which was the highest concentration which could be easily injected using a standard-bore syringe. µCT images of the H-MBP/PUR void filler injected into the femoral plug defects are shown in FIG. 9. For the images shown in FIGS. 9A-B, the wound was immediately closed after injection, while for the images in FIGS. 9 C-D, the wound was closed 15 minutes after injection. Allograft within the composite, as well as evidence of new bone formation, can be seen in the materials. While the sample size is too small (n=2) to assess the statistical significance, the two wound closure times do not appear to resulting in appreciable differences in bone content.

Figures 10A, 10B:
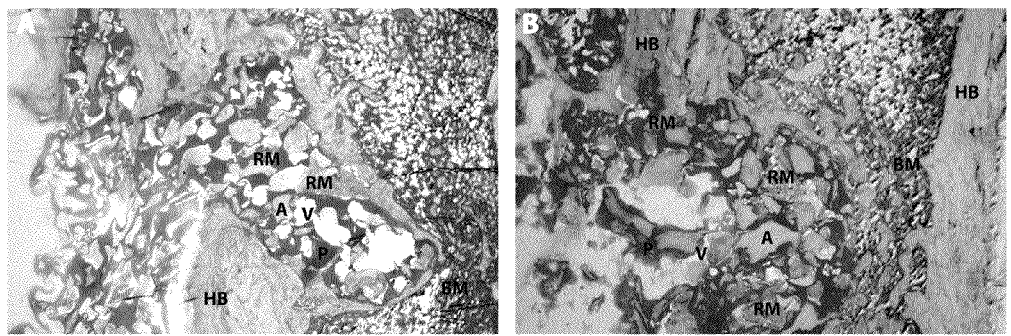
FIG. 10 illustrates thin (e.g., 4-6 μm) decalcified sections of the composite bone void filler injected in bilateral femoral plug defects in rats stained with fuchsin red-toluidene blue. (A)-(C): Low magnification images showing host bone (labeled "HB", light gray), residual polymer (labeled "P", dark gray), allograft particles embedded in polymer that have not been resorbed (labeled "A", light gray), regions of active remodeling (labeled "RM", medium gray) into the interior of the composite, osteoid (labeled "O", medium gray), and bone marrow (labeled "BM", medium gray) around the surface of the material. Panel (A) corresponds to the case where the wound was closed immediately after injection of the material, while Panels (B) and (C) correspond to the case where the wound was closed 15 minutes after injection. (D)-(F): Higher magnification views of the implant shown in Panel (C). (G)-(H) Higher magnification of regions of active remodeling characterized by allograft (light gray) resorption, cells (dark gray), and collagen deposition (medium gray). Panel (G) shows the cellular pathway in an interior region of the composite, while Panel (H) shows the infiltration of cells into the composite from the bone marrow. In the center of Panel (H) there is an allograft particle undergoing active remodeling that appears to be embedded in polymer except for a small breach (labeled "B") where cells infiltrated along the allograft/polymer interface.
Figures 10C, 10D, 10E, 10F:
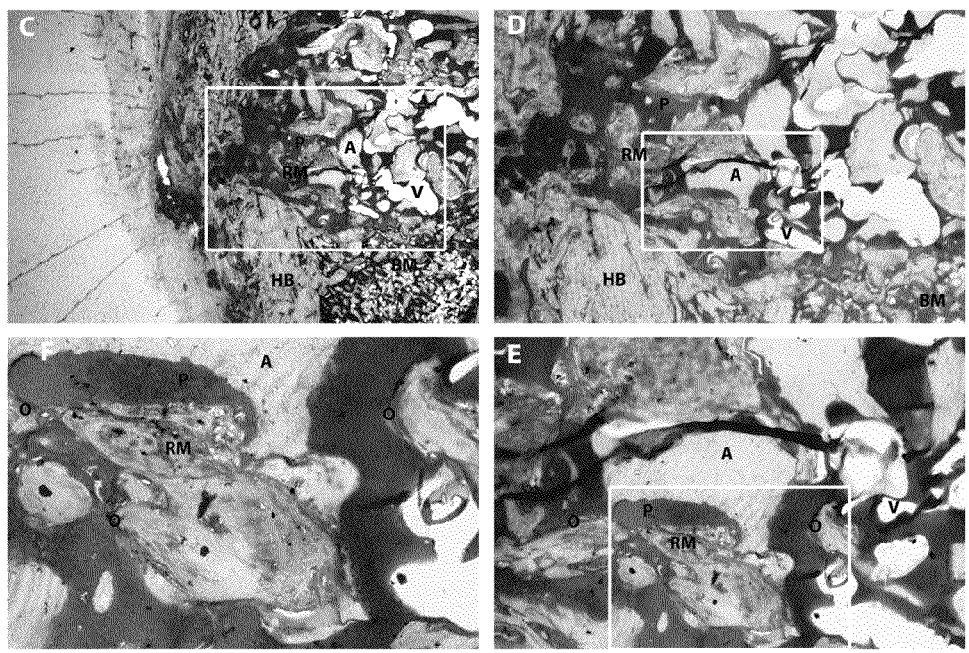
Figures 10G, 10H:
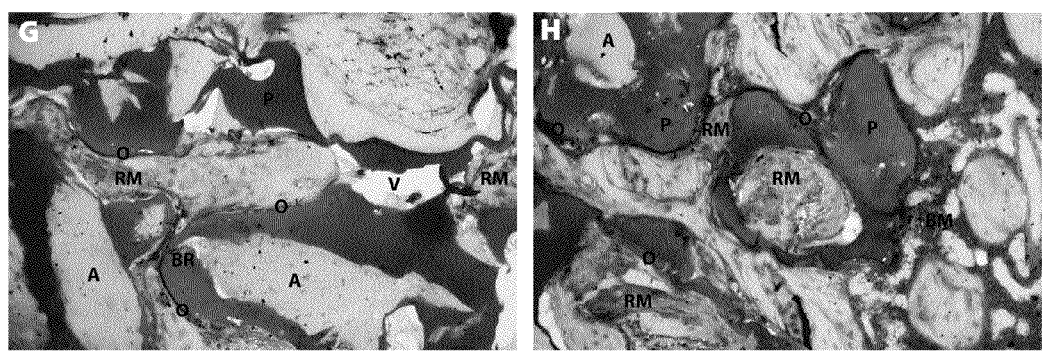
Figures 11A, 11B, 11C, 11D, 11E:
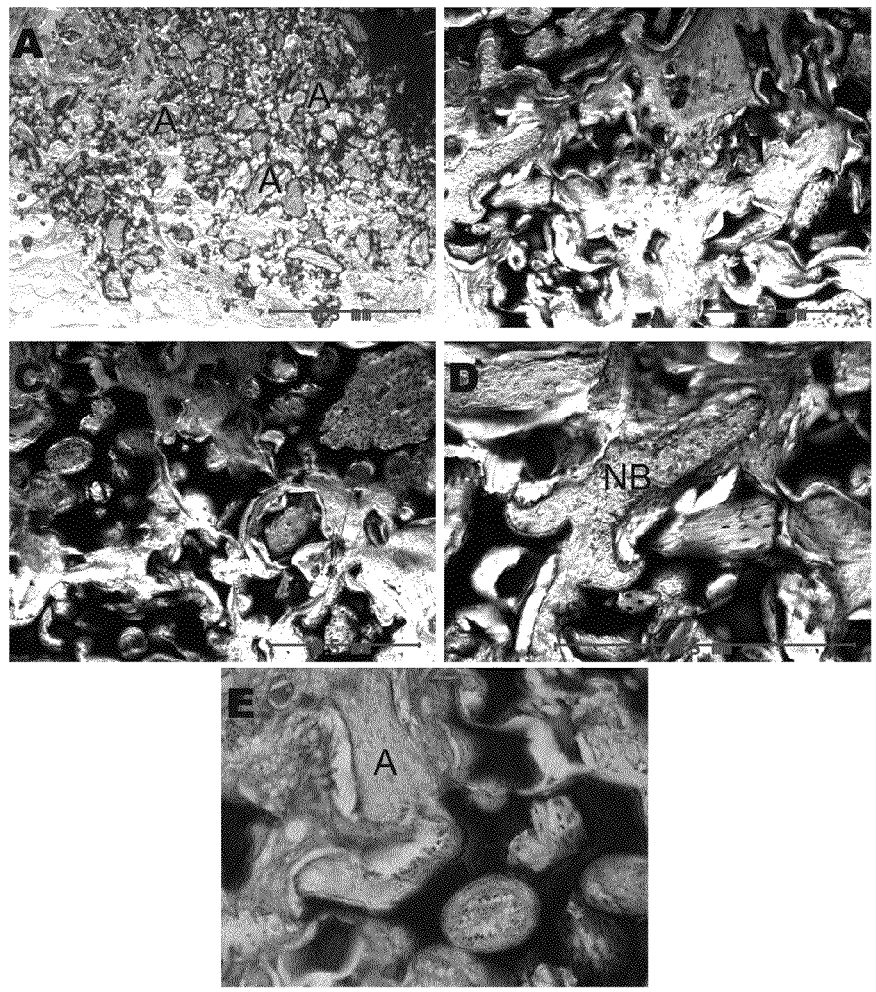
As shown in FIG. 11A, the boundary between the host bone and the implant is ambiguous. Extensive allograft bone resorption has occurred in this region near the host bone. The combination of pores and pathways resulting from allograft bone resorption facilitated the infiltration of cells into the implant. Higher magnification micrographs (FIGS. 11B-11E) further show cellular infiltration around remnants of polymer.
FIG. 11D shows new bone formation around a piece of allograft as evident by osteoid lining the surface.
FIG. 11E shows extensive resorption of an allograft particle along with mineralization inside a pore.

Thin (e.g., 4-6 µm) decalcified sections stained with fuchsin red/toluidine blue mixture are shown in FIG. 10. Panel A corresponds to the case where the material was injected and the wound immediately closed, while Panels B and C correspond to the case where the wound was closed 15 minutes after injection. Panels D, E, and F are higher magnification views of the material shown in Panel C. Polymer is stained red, unresorbed allograft and cortical bone are stained light pink, nuclei are stained purple, and collagen and connective tissue are stained blue. Direct apposition of the polymer (labeled "P") against the host bone (labeled "HB") surface is evident in the histological sections, suggesting that the injected composite established close contact with the host tissue. There is evidence of new bone growth adjacent to the material, as well as regions of active remodeling (labeled "RM") near the host bone/composite interface and also deep into the interior of the composite. These regions of active remodeling exhibit evidence of allograft resorption, osteoid (O) formation, collagen deposition, and new bone formation. While there is extensive remodeling of allograft particles throughout the composites, some of the allograft particles (labeled "A") were embedded in the polymer and thus did not remodel.

Cells appeared to infiltrate the material both by entering open pores (labeled "V"), as well as via resorption of allograft particles, as shown in Panels G and H. Panel G shows the cellular pathway in an interior region of the composite, while Panel (H) shows the infiltration of cells near the composite/host bone interface, where cells from the marrow (labeled "BM") are observed to migrate into the composite. In the center of Panel (H) there is an allograft particle undergoing active remodeling that appears to be embedded in polymer except for a small breach (labeled "B") where cells infiltrated along the allograft/polymer interface. Similarly, Panels E and F show a large allograft particle that appears to be embedded in polymer except for two breaches where cells have begun to infiltrate along the allograft/polymer interface. These observations suggest that resorption of the allograft creates pores into which cells subsequently migrate, thereby presenting an alternative pathway (in addition to migration through open pores) by which cells can infiltrate the composite.

Injectable biomaterials enable the filling of irregularly-shaped defects using minimally-invasive procedures. Injectable calcium phosphate bone cements, such as Norian SRS® (Synthes), have received FDA approval as a bone void filler for orthopaedic applications. In contrast to poly(methyl methacrylate) (PMMA), calcium phosphate cements are osteoconductive and biodegradable have been shown to support bone ingrowth in vivo. However, due to the small pore size (e.g., on the order of 1 µm), the rate of cellular infiltration is slow (Chim et al., *J Craniofac Surg* 2009; 20:29-33; Hollier et al., *Clin Plastic Surg* 2004; 31:423-428.), and the materials are prone to brittle fracture which can lead to infectious complications (Moreira-Gonzalez et al., *J Craniofac Surg* 2003; 14:144-153; United States Food and Drug Administration Center for Devices and Radiological Health, Manufacturer and User Facility Device Experience Database. Available at http://www.fda.gov/cdrh/maude.html. Accessed Nov. 5, 2008; Baker et al., *Plast Reconstr Surg* 2002; 109:1789-1796). In this study, an injectable bone void filler comprising allograft bone particles and a reactive, biodegradable polyurethane binder, has been developed. By varying the amount of water added, the porosity of the composites ranged from <5 to 70%. The working and tack-free times were adjusted by varying the concentrations of the tertiary amine catalysts, and varied from 4-8 min for the working time and from 10-20 min for the tack-free time (analogous to the setting time of a calcium phosphate cement).

As shown in FIG. 2, the composition of the surface of the allograft particles has a dramatic effect on the porosity. For SDMBP, the porosity approaches 50% even at very high water contents (8 pphp) in the absence of DMAEE, while for DFMBP, 50% porosity is attained at modest (4 pphp) water content. Furthermore, addition of the DMAEE blowing catalyst is required to increase the porosity of SDMBP composites above 50%. Demineralized bone matrix (DBM) is well-known to be significantly more hygroscopic than allograft bone. Therefore, the process of surface demineralization, is conjectured to present a hygroscopic surface that serves as a water sink in vivo. Water sensitivity should be considered when using such materials in surgery, as blood present in the defect before the scaffold is fully cured could have a significant effect on the porosity, and the on the mechanical properties and rate of remodeling as well.

The compressive stress-strain curves show that the 50 wt % SDBP/PUR scaffolds, with the exception of the wet 60% porosity scaffold, exhibited elastomeric properties up to 50% strain. The mechanical properties of the composites generally decreased after immersion in saline for 24 hours. In particular, the 60% porosity scaffolds were substantially weaker and failed under mechanical loading at strains less than 50%. This is in agreement with a previous study reporting that the organic/inorganic interfacial bonding strength for composites comprising biodegradable polymers and hydroxyapatite could be reduced by 80-90% after 30 hours in a humid environment (Neuendorf et al., Acta Biomater 2008; 4:1288-1296). Swelling of the allograft component is also conjectured to contribute to the reduction in mechanical properties at >50 vol % allograft.

The tack-free (e.g., setting) times of the injectable composites were tunable in the range of 10-20 minutes by reducing the TEDA concentration from 0.8 to 0.4 pphp (FIG. 6). A short setting time is clinically desirable, since in many cases the wound cannot be closed until the material has sufficiently cured to preserve its shape and morphology. The TEDA catalyst concentration also controlled the working time of the composites, which ranged from 4-8 minutes. Clinically, it is desirable to maximize the working time and minimize the setting time to facilitate handling in the operating room. As shown in FIG. 6, the working and setting times were related and decreased with increasing TEDA concentration. The difference between the working and setting times also decreased with increasing TEDA concentration. The allograft composition had a negligible effect on working and setting times, which is not surprising due to the fact that the onset of the gel point in the polymer network depends primarily on the polymerization reaction (Sperling L H. *Introduction to Physical Polymer Science*. New York: Wiley-Interscience; 2001). Thus the cure properties of the allograft/PUR composites were comparable to the working (6-10 min) and setting (10-15 min) time requirements reported for injectable bone cements and void fillers (Clarkin et al., *J Mater Sci: Mater Med* 2009; 20:1563-1570; Lewis et al., *J Biomed Mater Res Part B: Appl Biomater* 2007; 81B:371-386). Furthermore, the effects of wound closure time did not appear to significantly affect new bone growth and cellular infiltration, which suggests that the waiting period after injecting the material may be shortened by closing the wound prior to the setting time.

After 14 weeks (98 days) incubation time in saline, the SDMBP/PUR composites (ranging from 30-70% porosity) retained 86-92% of their initial weight. The degradation time of the composites was slower than that measured for the pure polymer scaffold (~50% of initial weight remaining after 14 weeks in vitro) due to both lower porosity as well as the allograft component, which does not degrade in saline. Interestingly, the allograft composites degraded significantly faster than porous PUR/TCP composites reported previously, where >95% of the material remained after 14 weeks incubation time in saline despite the lower TCP content (<10 vol %) (Adhikari et al., *Biomaterials* 2008; 29(28):3762-70). The slower degradation time of the TCP composites is conjectured to result from the slower degradation rate of the polymer component (Bonzani et al., *Biomaterials* 2007; 28:423-33; Hafeman et al., *Pharm Res* 2008; 25(10):2387-99).

Previous studies have shown that non-porous allograft/polymer composites exhibit extensive cellular infiltration into the interior, as well as modest new bone formation, when implanted in femoral condyle plugs in rabbits (Boyce et al., *Cellular Penetration And Bone Formation Depends Upon Allograft Bone Fraction In A Loadbearing Composite Implant.* 2005. p 133). Cellular infiltration was dramatically accelerated when the bone volume fraction approached the random close-packing (RCP) limit (64 vol %), resulting in multiple allograft particle-particle contacts which presented a continuous osteoconductive surface through the implant. In contrast, for PLLA/HA composites where the HA component was <40 wt % (~18 vol %), the rate of cellular infiltration and new bone formation was very slow (e.g., 5-7 years) and dependent on the rate of polymer degradation (Hasegawa et al., *Biomaterials* 2006; 27:1327-1332). Histological sections of allograft/polymer composites suggested that the allograft particles also functioned as a porogen, wherein osteoclast-mediated resorption of the allograft created pores in the implant into which osteoblasts migrated and deposited new bone. Thus, it is believed that a combination of allograft particles and pores would facilitate rapid cellular infiltration and remodeling of the implant, while providing sufficiently high initial mechanical properties comparable to those of calcium phosphate-based bone cements as well as trabecular bone.

Two-component PUR/TCP porous and non-porous composites have been reported to exhibit polymer degradation and new bone formation when implanted or injected into 6×12 m bilateral diaphyseal cortical defects in the femurs of skeletally mature Merino wether sheep (Adhikari et al., *Biomaterials* 2008; 29(28):3762-70). The yield strength varied from 6-13 MPa and the modulus from 270-580 MPa; these mechanical properties are comparable to the PUR/allograft composites of the present study. The materials implanted or injected in the sheep femoral plug defects exhibited either 42 or 55% porosity, and in one case incorporated 20 wt % (8.8 vol %) 5 µm TCP. New bone formation and osteogenic tissue were observed within the initial pores, as well as in the voids resulting from polymer degradation. New bone formation progressively advanced towards the center of the materials with increasing implantation time (e.g., from 6 to 24 weeks), and cellular infiltration and new bone formation were faster in faster degrading materials relative to slower degrading materials. Additionally, while the 5 µm TCP particles effectively reinforced the mechanical properties of the composites, their small size precluded remodeling by creeping substitution (Malinin et al., *Open Orthop J* 2007; 1:19-24). Taken together, these observations suggest that the rates of cellular infiltration and new bone formation were controlled by the rate of polymer degradation. In contrast, the PUR/allograft composites of the present study exhibited allograft resorption, cellular infiltration, collagen deposition, and new bone formation in the interior of the implant as early as 3 weeks. Considering the large amount of polymer remaining throughout the composite, it is unlikely that the rapid remodeling could be attributed to polymer degradation. The histological sections (FIG. 10) suggest that allograft remodeling by creeping substitution presented an alternative pathway for cells to infiltrate the composite by migrating along the allograft/polymer interface. These observations suggest that a continuous path for cellular migration into the interior of the implant may be achieved by a combination of open pores and allograft particles that are in the desirable size range (e.g., >100 µm) for remodeling by creeping substitution.

Injectable, biodegradable allograft bone/polyurethane composite scaffolds have been synthesized with tunable porosities, mechanical properties, degradation rates, and setting and working times that are comparable to those of calcium phosphate bone cements. Increasing the allograft content while maintaining porosity would accelerate cellular infiltration into the composites through both migration of cells into open pores, as well as remodeling of allograft particles by creeping substitution. When injected in femoral plug defects in athymic rats, the composites supported extensive cellular infiltration, allograft resorption, collagen deposition, and new bone formation at three weeks. The combination of both initial mechanical properties suitable for weight-bearing applications, as well as the ability of the materials to undergo rapid cellular infiltration and remodeling, may present potentially compelling opportunities for injectable allograft/polyurethane composites as biomedical devices for bone regeneration.

Example 8

Histological Evaluation

Components of a rabbit MBP/polyurethane composite were mixed, wherein the appropriate amounts of Tegoamin 33, polyester triol (comprising 60% ε-caprolactone, 30% glycolide, and 10% DL-lactide), rabbit MBP, and LTI-PEG prepolymer were added to a 10 mL cup and mixed using a Hauschild SpeedMixer (FlackTek, Inc., Landrum, S.C.). All composites incorporated 50 wt % (66.2 vol %) allograft bone and 60% porosity. The reactive paste was injected into a cylindrical mold, de-molded to yield a green cylinder (6.1 mm diameter).

Two New Zealand White (NZW) rabbits weighing between 3.8 and 4.1 kg were used in this study. All surgical and care procedures were carried out under aseptic conditions per the approved IACUC protocol. Rabbit MBP/PUR composite plugs were irradiated using a dose of approximately 25 kGY. Glycopyrrolate was administered at 0.01 mg/kg IM followed by ketamine at 40 mg/kg IM. Bilateral defects of approximately 6.1 mm diameter by 11 mm in depth were drilled in the metaphysis of the distal femurs of each rabbit. MBP/PUR plugs (n=2) and surface-demineralized bone/PUR plugs were subsequently inserted into each defect. Treatment groups for each composite were dispersed randomly among the rabbits. The rabbits were euthanized after six weeks using Fatal-plus (2.2 mL/10 kg) intra-venously. After 6 weeks' implantation time, the femurs were extracted and placed in a 1× phosphate buffer solution for 2 hours followed by dehydration in a series of ethanol and fixation in 10% formalin for 3 weeks.

A Faxitron LX-60 x-ray system was used to acquire micrographs of the extracted femurs after the PBS wash. Micrographs of each femur were taken at 40 kV with an exposure time 10 s. After fixation, the femurs were embedded in Technovit 7200 and 200-μm sections were cut from the resulting blocks using an Exakt band saw. The sections were then ground and polished using an Exakt grinding system to less than 100 μm and stained with Sanderson's rapid bone stain counterstained with van Gieson. In grayscale, old allograft is stained light gray, polymer is stained black, and cells are stained dark gray.

All of the histological micrographs suggest that the rabbit PUR/MBP composite plugs were biocompatible, as evidenced by the absence of a significant inflammatory response. Furthermore, the composites did not disrupt the normal wound healing process, as evidenced by the presence of osteoid lining the host bone surrounding the implant. As shown in Figure A, the boundary between the host bone and the implant is ambiguous. Extensive allograft bone resorption has occurred in this region near the host bone. The combination of pores and pathways resulting from allograft bone resorption facilitated the infiltration of cells into the implant. Higher magnification micrographs (Figures B-E) further show cellular infiltration around remnants of polymer. Figure D shows new bone formation around a piece of allograft as evident by osteoid lining the surface. Figure E shows extensive resorption of an allograft particle along with mineralization inside a pore.

All references, such as patents, patent applications, and publications, referred to above are incorporated by reference in their entirety.

Other embodiments are within the scope of the following claims.

What is claimed is:

1. A biodegradable composite, comprising:
   a plurality of bone particles;
   a NCO-terminated prepolymer, the NCO-terminated prepolymer comprising a polyisocyanate that includes about 10 wt % to about 55 wt % NCO and a first polyol that includes a molecular weight of about 100 g/mol to about 1000 g/mol; and
   a second polyol;
   wherein the composite in a hardened state is biodegradable and has a porosity of at least 3%.

2. The composite of claim 1, wherein the bone particles comprise cortical bone, cancellous bone, cortico-cancellous bone, or combinations thereof.

3. The composite of claim 1, wherein the bone particles comprise autogenous bone, allogenic bone, xenogenic bone, or combinations thereof.

4. The composite of claim 1, wherein the bone particles are nondemineralized, superficially, partially or fully demineralized.

5. The composite of claim 1, wherein the bone particles are surface demineralized.

6. The composite of claim 1, comprising at least approximately 40 wt %, 45 wt %, 50 wt %, 55 wt %, 60 wt %, 70 wt %, 80 wt %, or 90 wt % of bone particles.

7. The composite of claim 1, comprising at least approximately 30 vol %, 35 vol %, 40 vol %, 50 vol %, or 60 vol % of bone particles.

8. The composite of claim 1, further comprising an inorganic material.

9. The composite of claim 8, wherein the inorganic material is selected from the group consisting of aragonite, dahlite, calcite, amorphous calcium carbonate, vaterite, weddellite, whewellite, struvite, urate, ferrihydrite, francolite, monohydro calcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate (OCP), calcium phosphate silica glass, fluoroapatite, chloroapatite, magnesium substituted tricalcium phosphate, carbonate hydroxyapatite, and combinations and derivatives thereof.

10. The composite of claim 1, further comprising one or more of serum albumin, collagen, an extracellular matrix component, a synthetic polymer, and a naturally-derived polymer.

11. The composite of claim 1, wherein the second polyol comprises a polymer selected from the group consisting of poly(caprolactones), poly(lactide), poly(glycolide), polyglyconate, poly(arylates), poly(anhydrides), poly(hydroxy acids), polyesters, poly(ortho esters), poly(alkylene oxides), polycarbonates, poly(propylene fumarates), poly(propylene glycol-co fumaric acid), polyamides, polyethers, polyureas, polyamines, polyamino acids, polyacetals, poly(orthoesters), poly(pyrolic acid), poly(glaxanone), poly(phosphazenes), poly(organophosphazene), polylactides, polyglycolides, poly(dioxanones), polyhydroxybutyrate, polyhydroxyvalyrate, polyhydroxybutyrate/valerate copolymers, poly(vinyl pyrrolidone), polycyanoacrylates, polyurethanes, polysaccharides, and combinations thereof.

12. The composite of claim 1, wherein the second polyol comprises poly(caprolactone), poly(lactide), poly(glycolide), and/or combinations thereof.

13. The composite of claim 1, further comprising a porogen.

14. The composite of claim 1, further comprising a bioactive agent.

15. The composite of claim 14, wherein the bioactive agent is selected from the group consisting of antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, and penetraction enhancer.

16. The composite of claim 1, wherein the porosity is at least about 30%, at least about 40%, at least about 50%, at least about 60%, at least about 70%, at least about 80%, or at least about 90%.

17. The composite of claim 1, wherein the porosity is in a range of 30% to 45%.

18. The composite of claim 1, wherein the composite comprises pores or channels that can support the in-growth of cells after implantation.

19. The composite of claim 1, wherein the second polyol is a polyester polyol.

20. The composite of claim 1, being configured for the repair of a simple fracture, compound fracture or non-union; as an external fixation device or internal fixation device; for joint reconstruction, arthrodesis, arthroplasty or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; for revision surgery; for revision surgery of a total joint arthroplasty; and for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones or metatarsal bones.

21. The composite of claim 1, wherein the polyisocyanate comprises lysine triisocyanate (LTI).

22. The composite of claim 21, wherein the first polyol comprises PEG.

23. The composite of claim 1, wherein the NCO-terminated prepolymer comprises about 14 wt % to about 26 wt % NCO.

24. The composite of claim 1, wherein the NCO-terminated prepolymer comprises about 23 wt % NCO.

25. The composite of claim 1, wherein the NCO-terminated prepolymer comprises a viscosity of about 21,000 cP.

26. The composite of claim 1, further comprising a polysaccharide filler.

27. The composite of claim 26, wherein the polysaccharide filler comprises hyaluronic acid (HA), carboxymethylcellulose (CMC), or combinations thereof.

28. The composite of claim 26, comprising about 10 wt % to about 35 wt % of the polysaccharide filler.

29. The composite of claim 1, wherein the first polyol is the same as the second polyol.

30. The composite of claim 1, further comprising a catalyst.

31. The composite of claim 1, wherein the first polyol is a polyether polyol.

32. A biodegradable composite, comprising:
a plurality of bone particles;
a biodegradable polymer that includes a NCO-terminated prepolymer, the NCO-terminated prepolymer including a polyisocyanate and a first polyol, and a second polyol; and
wherein the composite in a hardened state is biodegradable and has a porosity of at least 3%.

* * * * *